United States Patent

Karlson et al.

[11] Patent Number: 5,991,048
[45] Date of Patent: Nov. 23, 1999

[54] SURFACE PLASMON RESONANCE LIGHT PIPE SENSOR

[75] Inventors: Scott Karlson, Mountlake Terrace; Sinclair S. Yee, Seattle; Kyle Johnston, Bothell; Ralph Jorgenson, Seattle, all of Wash.

[73] Assignee: University of Washington, Seattle, Wash.

[21] Appl. No.: 08/738,360

[22] Filed: Oct. 25, 1996

Related U.S. Application Data

[60] Provisional application No. 60/007,027, Oct. 25, 1995, provisional application No. 60/005,878, Oct. 26, 1995, and provisional application No. 60/009,169, Dec. 22, 1995.

[51] Int. Cl.$^6$ .................................................. G01N 21/55
[52] U.S. Cl. ........................................................... 356/445
[58] Field of Search .................................. 356/445–448, 356/128; 385/12, 13

[56] References Cited

U.S. PATENT DOCUMENTS

| | | |
|---|---|---|
| 4,844,613 | 7/1989 | Batchelder et al. . |
| 4,889,427 | 12/1989 | Van Veen et al. . |
| 4,997,278 | 3/1991 | Finlan et al. . |
| 5,055,265 | 10/1991 | Finlan . |
| 5,064,619 | 11/1991 | Finlan . |
| 5,120,131 | 6/1992 | Lukosz . |
| 5,313,264 | 5/1994 | Ivarsson et al. . |
| 5,327,225 | 7/1994 | Bender et al. . |
| 5,351,127 | 9/1994 | King et al. . |
| 5,359,681 | 10/1994 | Jorgenson et al. . |
| 5,374,563 | 12/1994 | Maule . |
| 5,425,124 | 6/1995 | McRight et al. . |
| 5,474,815 | 12/1995 | Sunderland . |
| 5,478,755 | 12/1995 | Attridge et al. . |
| 5,485,277 | 1/1996 | Foster . |
| 5,492,840 | 2/1996 | Malmqvist et al. . |

FOREIGN PATENT DOCUMENTS

| | | |
|---|---|---|
| 2174802 | 11/1986 | United Kingdom . |
| 2186387 | 8/1987 | United Kingdom . |
| 2247749 | 3/1992 | United Kingdom . |
| WO88/08992 | 11/1988 | WIPO . |
| WO89/07756 | 8/1989 | WIPO . |

OTHER PUBLICATIONS

Bussjager, R. and Macloud, H. (1995), "The inverted surface plasmon resonance: further discussion," *J. Modern Optics* 42(7):1355–1360.

(List continued on next page.)

*Primary Examiner*—K P Hantis
*Attorney, Agent, or Firm*—Greenlee, Winner & Sullivan, P.C.

[57] ABSTRACT

The present invention provides SPR sensors in which the sensing element is a planar lightpipe. The sensors of this invention include configurations which employ multiwavelength light incident on the SPR sensing area at a single angle or at a range of angles. Sensors of this invention also include configurations that employ monochromatic light at a range of angles. Many of the configurations of the SPR lightpipe sensors of this invention involve imaging of input light through the lightpipe. In one embodiment, the invention provides a first order SPR sensor system in which the sensing element is a planar lightpipe. Light coupled into the lightpipe reflects off an SPR sensing area positioned on an external surface planar surface of the lightpipe. Multiwavelength light that is coupled into the lightpipe input face at a range of angles propagates through the lightpipe by total internal reflection (TIR), making multiple reflections, and exits in a series of angular bands each containing spectral information (including SPR features)for a small range of incidence angles. A detector or detectors are positioned to measure the reflection spectrum, including any surface plasmon resonance feature, of one or preferably more than one of the angular bands exiting the lightpipe. SPR sensor configurations include those that have multiple sensing channels and those which can be multiplexed. This invention provides SPR sensors with planar lightpipe sensing elements and method of detecting analytes in samples using these sensors. The invention also provides planar lightpipe that have a plurality of SPR sensing layers on a planar surface.

46 Claims, 13 Drawing Sheets

OTHER PUBLICATIONS

Gordon, J.G and Ernst, S. (1980), "Surface Plasmons as a Probe of the Electrochemical Interface," *Surf. Sci. 101*:499–506.

Ishimaru, A. *Electromagnetic Wave Propagation, Radiation, and Scattering,* Prentice Hall, Englewood Cliffs, NJ (1991) Chapter 3 pp. 43–45.

Johnston, K.S. et al (1995), "New analytical technique for characterization of thin films using surface plasmon resonance," *Mater. Chem. Phys.* 42:242–246.

Jorgenson, R.C. and Yee, S.S. (1993) "A Fiber Optic Chemical Sensor Based on Surface Plasmon Resonance," *Sensors and Actuators B* 12:213–220.

Jorgenson, R.C. and Yee, S.S. (1994) "Control of the Dynamic Range and Sensitivity of a Surface Plasmon Resonance Based Fiber Optic Sensor" *Sensors and Actuators A 43*:44–48.

Jory, M.J. et al. (1994), "Development of a prototype gas sensor using surface plasmon resonance on gratings," *Sensors and Actuators B* 17:203–209.

Jung, C. (1991), "Surface Plasmon Resonance," Master Thesis, University of Washington.

Jung, C. et al. (1995), "Electro–optic polymer light modulator based on surface plasmon resonance," *Appl. Opt.*34(6):946–949.

Jung, C.C. et al. (1995) "Fiber–Optic Surface Plasmon Dispersive Index Sensor for Highly Opaque Samples" *Process Control and Quality 7:*167–171.

Karlsen, S.R. et al. (1995), "Simultaneous Determination of Refractive Index and Absorbance Spectra of Chemical Samples Using Surface Plasmon Resonance," *Sensors and Actuators B* 24–25:747–749.

Kretschmann, E. and Raether, H. (1968) "Radiative Decay of Non–radiative Surface Plasmons Excited by Light" *Z. Naturforsch., Teil A,* 23: 2135–2136.

Kreuwel, H.J.M. et al. (1987) "Surface Plasmon Dispersion and Luminescence Quenching Applied to Planar Waveguide Sensors for the Measurement of Chemical Concentrations," *Proc. SPIE* 798:218–224.

Lambeck, P.V. (1992) "Integrated Opto–Chemical Sensors" *Sensors and Actuators B* 8:103–116.

Lavers, C.R. and Wilkinson, J.S. (1994), "A waveguide–coupled surface–plasmon sensor for an aqueous environment," *Sensors and Actuators B* 22:75–81.

Liedberg, B. et al. (1983), "Surface plasmon resonance for gas detection and biosensing," presented at Solid–State Transducers 83, Delft, The Netherlands, May 31–Jun. 3, 1983, p. 299–304.

Mar, M. et al. (1993) "In–Situ Characterization of Multilayered Langmuir–Blodgett Films Using a Surface Plasmon Resonance Fiber Optic Sensor" Proc. of the 15th Annual Conf. of the IEEE Engineering in Medicine and Biology Soc., San Diego, CA pp. 1551–1552.

Nelson, S.G. et al. (1996) "High Sensitivity Surface Plasmon Resonance Sensor Based on Phase Detection" presented at the Sixth International Conference on Chemical Sensors (Jul. 22–24, 1996) Washington, D.C.

Pockrand, I. et al. (1979) "Exciton–Surface Plasmon Interactions" *J. Chem. Phys.* 70:3401–3408.

Printz, M. et al. (1993), "An inverted surface plasmon resonance," *J. Modern Optics 40* (11):2095–2104.

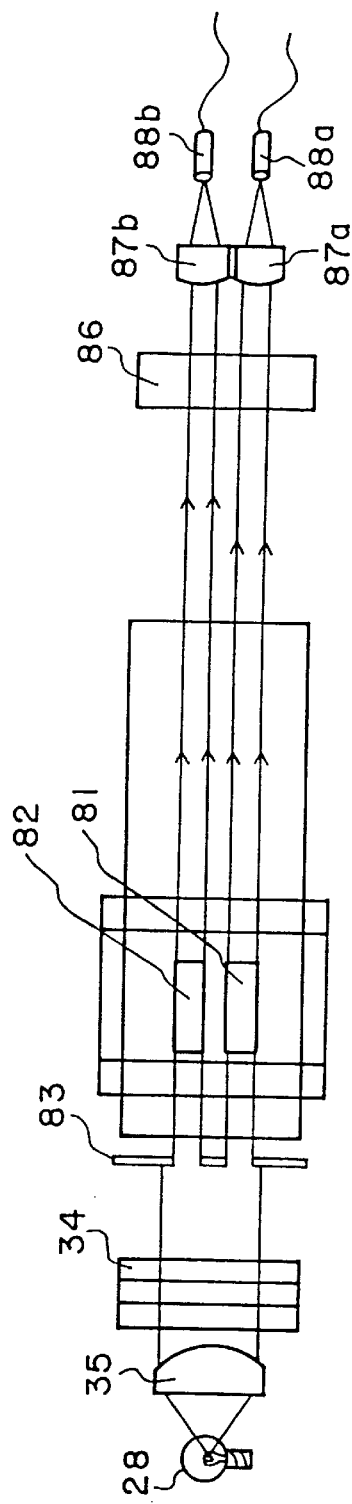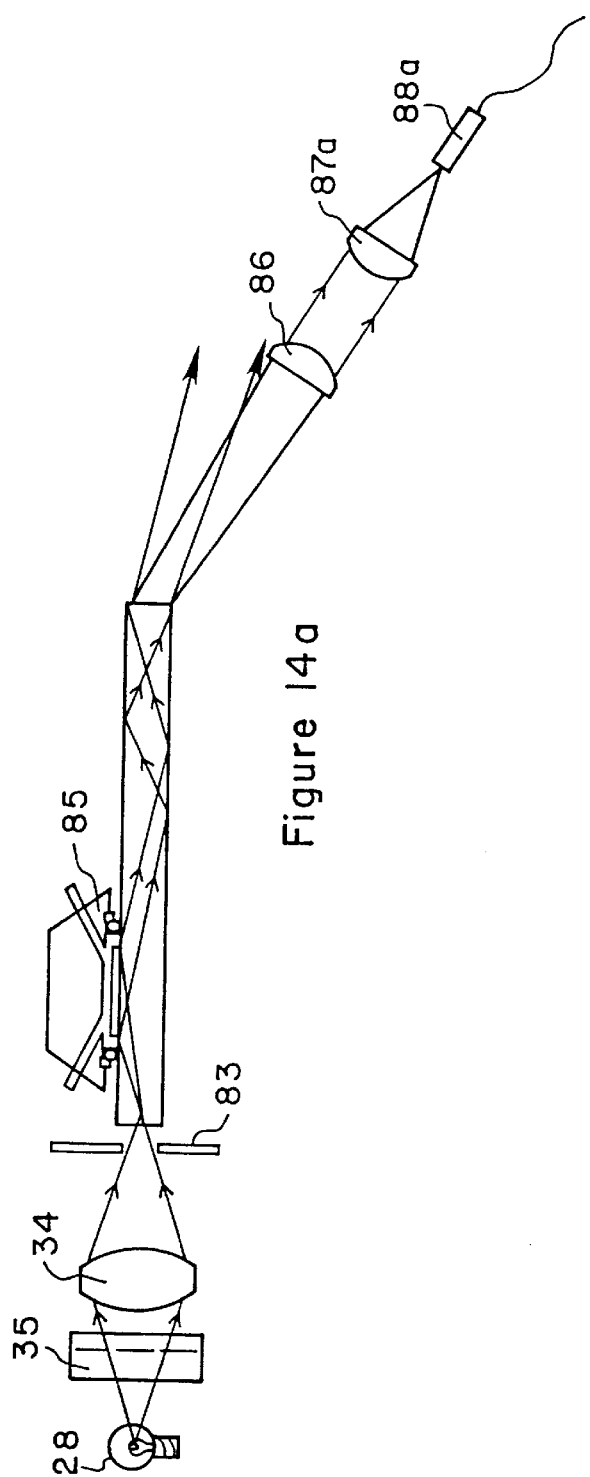

SURFACE PLASMON RESONANCE LIGHT PIPE SENSOR

CROSS-REFERENCE TO RELATED APPLICATIONS

This application claims the benefit of priority under 35 U.S.C. 119(e) of U.S. provisional applications Ser. No. 60/007,027 filed Oct. 25, 1995; Ser. No. 60/005,878 filed Oct. 26, 1995; and Ser. No. 60/009,169 filed Dec. 22, 1995 all of which are incorporated in their entirety by reference herein.

This invention was made, at least in part, with support from the National Science Foundation under grant number EID-9212314. The United States Government has certain rights in this invention.

FIELD OF THE INVENTION

This invention relates in general to surface plasmon resonance sensors and more particularly to zero and first order sensors employing a planar lightpipe sensor configuration. Configurations of these sensors can be employed for either or both wavelength modulation or angular modulation SPR.

BACKGROUND OF THE INVENTION

Optical surface plasmon resonance (SPR) sensors are sensitive to changes in the refractive index (RI) of a sample near the sensor surface. Most bulk prism SPR sensor configurations measure either the angular reflection spectrum for monochromatic light or the wavelength reflection spectrum for collimated white light.

Various SPR sensor configurations utilizing waveguides, including optical fibers, have been reported. These include a single-mode planar waveguiding structure which detects intensity changes in monochromatic light (Lavers, C. R. and Wilkinson, J. S. (1994) "A Waveguide-Coupled Surface-Plasmon Sensor for an Aqueous Environment" *Sensors and Actuators B* 22:75–81) and a sensor system in which white light is injected into a single-mode waveguide having an SPR supporting superstructure (Kreuwel, H. J. M. et al. (1987) "Surface Plasmon Dispersion and Luminescence Quenching Applied to Planar Waveguide Sensors for the Measurement of Chemical Concentrations," *Proc. SPIE* 798:218–224; Lambeck, P. V. (1992) "Integrated Opto-Chemical Sensors" *Sensors and Actuators B* 8:103–116). Additionally, a white light multi-mode fiber optic SPR sensor has been introduced (U.S. Pat. No. 5,359,681, issued October 1994); Jorgenson, R. C. and Yee, S. S. (1993) "A Fiber Optic Chemical Sensor Based on Surface Plasmon Resonance," *Sensors and Actuators B* 12:213; Jung, C. C. et al. (1995) "Fiber-Optic Surface Plasmon Dispersive Index Sensor for Highly Opaque Samples" *Process Control and Quality* 7:167–171; Jorgenson, R. C. and Yee, S. S. (1994) "Control of the Dynamic Range and Sensitivity of a Surface Plasmon Resonance Based Fiber Optic Sensor" *Sensors and Actuators A* 43:4448; Mar, M. et al. (1993 ) "In-Situ Characterization of Multilayered Langmuir-Blodgett Films Using a Surface Plasmon Resonance Fiber Optic Sensor" Proc. of the 15th Annual Conf. of the IEEE Engineering in Medicine and Biology Soc., San Diego, Calif. pp. 1551–1552.

U.S. Pat. No. 5,485,277 (filed Jul. 26, 1994, issued Jan. 16, 1996) "Surface Plasmon Resonance Sensor and Methods for the Utilization Thereof " reports an SPR sensor said to comprise a "waveguide" cartridge, a cylindrical diverging lens coupled to the "waveguide" and a plurality of photodetectors optically connected to the cylindrical lens. The "waveguide", exemplified by a microscope slide with angled input and output faces, carries a symmetrically positioned metal layer that supports SPR. Apparently, monochromatic light is introduced into the "waveguide" through the angled polished input face by focusing the light through the end of the "waveguide" onto the metal sensor surface at a range of angles spanning angular location of the surface plasmon resonance. The angle of the input face of the "waveguide" is polished to an angle $\alpha_{wvg}$, where $$\tan \alpha_{wvg} = \tan \theta_{central} - \frac{\sec \theta_{central}}{n_{wvg}} \tag{1}$$

and $n_{wvg}$ is the refractive index of the "waveguide" and $\theta_{central}$ is the center angle of the range of rays directed at the sensing surface. It appears that $\theta_{central}$ is very close to $\theta_{SPR}$, the surface plasmon resonance angle. The RI of the sample is determined by measuring light intensity exiting the sensor as a function of angle. The patent also discusses the use of sensing and reference channels on the same metal film-coated waveguide.

SPR sensor waveguide configurations that have been reported are limited to those measuring refractive index at either a single wavelength or a single angle (angular or wavelength modulation, respectively). Such configurations are considered zero order sensors since they measure only one independent variable for a given analyte. Recently, a first order SPR sensor geometry that can simultaneously measure a sample's index of refraction at multiple wavelengths was reported (Karlsen, S. R. et al. (1995), "Simultaneous Determination of Refractive Index and Absorbance Spectra of Chemical Samples Using Surface Plasmon Resonance," *Sensors and Actuators B* 24–25:747–749). This dispersive RI sensor which employed a cylindrical sapphire prism with a gold sensing layer required several discrete optical components which introduced optical aberrations in the reflected signal, making it difficult to calibrate both the angular and spectral outputs of the sensor.

Thus there remains a need in the art for first order SPR sensors that allow independent measurements of two variables for a given analyte providing dispersive RI information and for SPR sensors allowing the simultaneous determination of two parameters, for example, film thickness and RI of a thin film applied to an SPR sensing surface. There is also a need in the art, particularly for assay of biological samples, for SPR sensors that can simultaneously detect more than one analyte in a sample (multiplexed sensors). There also generally remains a need for SPR sensors which are sensitive, simple to use, readily calibrated, compact in size and rugged, and inexpensive to produce. SPR sensors of this invention meet these needs.

SUMMARY OF THE INVENTION

The present invention provides SPR sensors in which the sensing element is a planar lightpipe. The sensors of this invention include configurations that employ multi-wavelength light (including broad band and white light) incident on the SPR sensing area at a single angle or at a range of angles. Sensors of this invention also include configurations that employ monochromatic light at a range of angles. Many of the configurations of the SPR lightpipes of this invention involve imaging of input light through the lightpipe.

In one general embodiment, the invention provides a first order SPR sensor system in which the sensing element is a planar lightpipe. Light coupled into the lightpipe reflects off an SPR sensing area on a planar surface of the lightpipe. The lightpipe sensor is distinct from previous waveguide systems in that ray tracing theory describes the propagation of light in and through the lightpipe at a range of angles. In contrast, light propagation in waveguides (either single- or multiple-mode) is described by mode theory. Non-monochromatic, i.e., multiwavelength, light that is coupled into the lightpipe input face at a range of angles propagates through the lightpipe by total internal reflection (TIR), making multiple reflections, and exits in a series of angular bands each containing spectral information (including SPR features) for a small range of incidence angles. A detector or detectors are positioned to measure the reflection spectrum, including any surface plasmon resonance feature, of one or preferably more than one of the angular bands exiting the lightpipe. The same sensor configuration can be employed to measure SPR from a range of incidence angles of monochromatic input light (simple angular modulation) or to measure SPR from a range of incidence angles of more than one wavelength. The measurement of a broad range of angles and wavelengths allows the measurement of a dispersive RI curve (i.e., RI as a function of wavelength) of a given sample or analyte.

The lightpipe SPR sensors of this invention have automatic angular calibration, minimal optical aberrations, and does not require index matching fluids. In one embodiment, a lightpipe sensor can be fabricated from inexpensive, disposable microscope slide, providing an SPR sensor which can measure dispersive RI of a sample in a simple, compact, and inexpensive manner.

Light can be coupled into and out of the lightpipe sensors of this invention in a variety of ways using conventional optical apparatus to focus, collimate and/or selectively expand light on coupling into the lightpipe or to focus, collimate, disperse, and/or collect light exiting the lightpipe. Incident light must comprise TM polarized light. The light employed in the sensor is optionally TM polarized to remove the TE component prior to launch into the sensor. Alternatively, the TE component light is removed by passage through a TM polarizer any time prior to detection.

The planar lightpipe of the sensors of this invention has at least one SPR sensing area on at least one of its planar surfaces. A SPR sensing area comprises an SPR-supporting conducting layer, preferably an SPR-supporting metal layer and optionally has an adherence layer, dynamic range-controlling layers and reactive layers. In particular embodiments, the SPR sensors of this invention can have a plurality of sensing areas across the width, along the length or both of a lightpipe surface. Lightpipes of the sensors of this invention can include both active and reference sensing areas and active sensing areas on a given lightpipe can have sensing areas specific for the same or different analytes in a sample.

SPR sensors of this invention can include static or flow sample cells to confine samples for SPR measurements. This invention includes multichannel and mutiplexed SPR sensors having a plurality of independent SPR sensing areas on a planar lightpipe surface. In addition, sample cells can be configured to contact different sensing areas on the lightpipe surface with different samples.

Lightpipes of the sensors of this invention can be fabricated from a variety of materials transparent or semi-transparent to the input light. Glass, crystal, including sapphire, as well as plastic and polymer materials can be used for the lightpipe substrate. Lightpipes optionally have a cladding layer to insure TIR of light along the length of the lightpipe.

SPR Lightpipe sensors of this invention can be employed as biosensors, particularly to detect multiple analytes in biological samples, such as serum or blood.

In a specific embodiment, a planar lightpipe sensor configured for single angle operation is provided. The lightpipe is beveled at selected angles at its input end or at both its input and output ends to facilitate coupling of substantially collimated white light, preferably TM polarized white light, at a selected single angle that excites SPR at the sensing area. Angle selection is made by bevel angle used. This embodiment is a zero order sensor in the sense that it allows measurement for a given analyte at only a single angle of incidence. In this embodiment, however, the lightpipe can have a plurality of SPR sensing areas across its width to provide for multichannel sensing. Refractive index sensitivity of this configuration is estimated as $4 \times 10^{-5}$ RI units.

This invention provides SPR sensors with planar lightpipe sensing elements and a method of detecting analytes in samples using these sensors. The invention also provides planar lightpipes that have a plurality of SPR sensing layers on a planar surface.

BRIEF DESCRIPTION OF THE FIGURES

FIGS. 14A and 14B illustrate a dual-channel configuration of the SPR sensor of FIG. 7 with symmetric light input. FIG. 14B is a top view showing the lateral placement of the two sensing areas. FIG. 14A is a side view of the sensor showing input and output optics.

DETAILED DESCRIPTION OF THE INVENTION

A surface plasmon wave is an electromagnetic wave which propagates along the interface between a conductor (or semi-conductor) and a dielectric, and decays normal to the interface. A plasmon is the collective oscillations of free charges, ions or valence electrons, in a metal or semi-conductor which can be excited by a polarizing interaction (a polaritron) between an electromagnetic wave and an oscillator resonant at the same frequency as the wave. A surface plasmon polaritron is the interaction between photons and the collective oscillations of electrons at the surface of a conductor. The interaction is strongest at the resonance condition known as surface plasmon resonance, which is satisfied when the tangential component of the wave vector of light incident on the conductor is equal to the wave vector of the surface plasmon wave. Incident light satisfying the resonance condition causes surface charges on the conductor to oscillate creating a bound electromagnetic or charge-density wave propagating along the interface between the conductor and a dielectric material. The resonance condition depends on the wavelength of incident light and the angle at which light is incident upon the interface as well as the dielectric constants of all of the materials in the layers involved, including that of a dielectric sample in contact with the sensing layer.

For the case in which a metal SPR-supporting layer on a supporting dielectric substrate (e.g., glass) is in contact with a dielectric sample, the resonance condition is:

$$k_x = k_o n_{substrate} \sin(\theta) = k_{sp}, \quad (2)$$

where $k_o = 2\pi/\lambda$ is the free space wave vector of the incident light, $\theta$ is the incident angle of the light, $n_{substrate}$ is the complex, wavelength-dependent refractive index (RI) of the substrate. The wave vector of surface plasmon wave, $k_{sp}$, can be approximated as (Jung, C. (1991), "Surface Plasmon Resonance," Master Thesis, University of Washington)

$$k_{sp} = k_0 \left[ \frac{\varepsilon_d \varepsilon_m}{\varepsilon_d + \varepsilon_m} \right]^{\frac{1}{2}} \quad (3)$$

where $\varepsilon_d$ and $\varepsilon_m$ are the wavelength dependent complex dielectric permitivities of the dielectric sample and metal.

In a sensing configuration, the excitation of SPR is detected as a decrease in the reflection coefficient (i.e., a decrease in intensity) of TM polarized light reflected off the sensing interface. See: Pockrand, I. et al. (1979) "Exciton-Surface Plasmon Interactions" *J. Chem. Phys.* 70:3401; Jorgenson and Yee (1993) supra. Plane-wave Fresnel reflection equations can be used to model the resonance condition for a sensing interface containing multiple planar layers. See: Ishimaru, A. *Electromagnetic Wave Propagation, Radiation, and Scattering,* Prentice Hall, Englewood Cliffs, N.J. (1991) Chapter 3 pp. 43–45.

Figure 1:
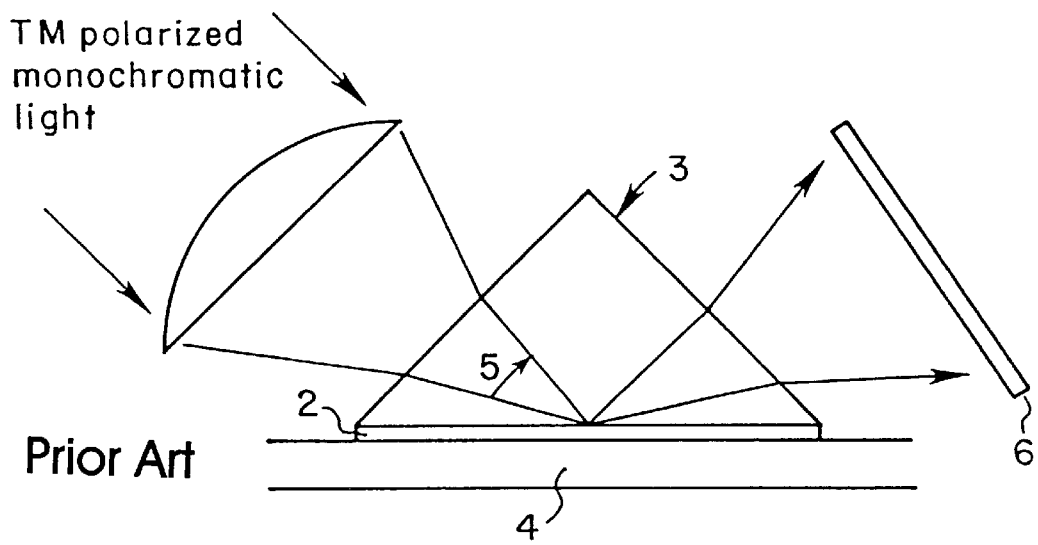
FIG. 1 is a schematic drawing of a prior art bulk prism angle modulated SPR sensor illustrating the Kretschmann configuration.
Figure 2:
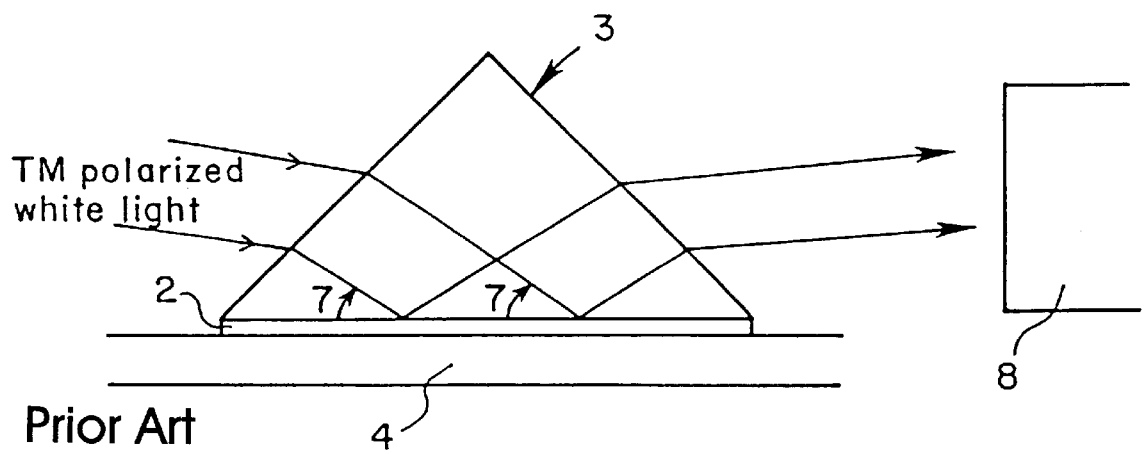
FIG. 2 is a schematic drawing of a prior art bulk prism wavelength modulated SPR sensor analogous to the Kretschmann configuration of FIG. 1.

Conventional SPR sensing techniques generally use either angle or wavelength modulation. These techniques are illustrated in FIGS. 1 and 2 for a Kretschmann configuration (Kretschmann, E. and Raether, H. (1968) "Radiative Decay of Non-radiative Surface Plasmons Excited by Light" *Z. Naturforsch., TeilA,* 23: 2135–2136) in which a thin, highly-reflective metal film (2) is deposited on the base of a prism (3). The metal layer is brought into contact with a solid, liquid or gas dielectric sample (4) creating a metal-dielectric interface that will support SPR. In the Kretschmann configuration of FIG. 1, TM-polarized monochromatic light is focused onto the back of the sensing surface (metal layer, 2) at a range of angles (5) and the intensity of the light reflected from the sensing surface is measured as a function of incidence angle, for example, using a linear array detector (6). This is angle modulation. FIG. 2 illustrates a wavelength modulated SPR sensor analogous to the Kretschmann configuration of FIG. 1. TM-polarized collimated white light is incident upon the sensing surface (2) at a single angle (7), and intensity of the light reflected from that surface is measured as a function of wavelength, for example, using a spectrograph (8). As stated above, resonance depends upon both the wavelength of incident light and the angle or angles at which the light hits the sensing interface (incidence angle(s)). These traditional zero order sensing techniques hold one variable (angle or wavelength) constant and measure the reflection coefficient as a function of the other variable. For angle modulated SPR at a fixed wavelength, there can be an angle $\theta_{SPR}$ that satisfies the resonance condition. For a fixed angle, there can be a wavelength $\lambda_{SPR}$ at which the wavelength dependent permitivities (or RI's) of the various media are such as to satisfy the resonance condition. The angle or wavelength at which resonance (i.e., minimum reflected light intensity) is observed gives a measure of the effective index of refraction (RI) of the dielectric sample. The resonant angle ($\theta_{spr}$) or wavelength ($\lambda_{spr}$) can be calibrated (using samples of known refractive index) to the refractive index of the sample.

Surface plasmon resonance sensors using only wavelength or angle modulation are considered zero order sensors because the vector of reflected intensities (I$\theta$) or I($\lambda$) is reduced to a single value of ($\theta_{spr}$) or ($\lambda_{spr}$). The previously reported bulk optic first order SPR sensor (Karlsen, S. R. et al. (1995), "Simultaneous determination of refractive index and absorbance spectra of chemical samples using surface plasmon resonance," *Sensors and Actuators B* 24–25:747–749) simultaneously monitored reflection coefficients over a range of angles and a range of wavelengths. This approach produces a matrix of data which can be reduced to a vector of RI values at different wavelengths.

The SPR excitation condition is extremely sensitive to the changes in the refractive index of the dielectric layers (e.g., substrate and sample) surrounding the SPR-supporting conductor sensing layer. The refractive index of a dielectric sample (in a sensor with a given substrate) can be detected by monitoring the SPR condition. Any shift in resonance curves ($\delta\theta_{spr}$ or $\delta\lambda_{spr}$) indicates a change in refractive index at the conductor/sample interface.

SPR measures the complex refractive index of the sample in contact with the sensing area of the lightpipe. This complex refractive index includes both the real and imaginary refractive index components. The real component is inversely proportional to the speed at which light propagates through the sample, and is generally considered the "true" refractive index of the sample. The imaginary component is related to the sample's absorbance or attenuation of light. SPR sensors can thus be used to measure the absorbance of a sample as well as its index of refraction.

The SPR sensors of this invention employ a planar lightpipe configuration for zero or first order sensor applications. As used herein the term lightpipe relates to a three dimensional structure that confines optical energy and allows it to be conducted from one point to another point with minimal loss by total internal reflection (TIR). The dimensions of a lightpipe are large in comparison to the wavelength of light to be confined and conducted therein, so that a lightpipe allows a continuous range of directions of light propagation within its boundaries. In addition, due to its relatively large dimensions the propagation of light within a lightpipe can be modeled using ray theory rather than mode theory. In contrast to a lightpipe, a waveguide is a three dimensional structure that confines and conducts light having dimensions comparable to the wavelength of light it confines and conducts. Light in a waveguide retains modal properties; it may be single-mode or multi-mode, but the allowed wave vector values are not continuous as in a lightpipe. The propagation of light in a waveguide, except when there are a very large number of modes, i.e., when the waveguide is almost a lightpipe, can be modeled using mode theory but not ray theory.

Figure 3A:
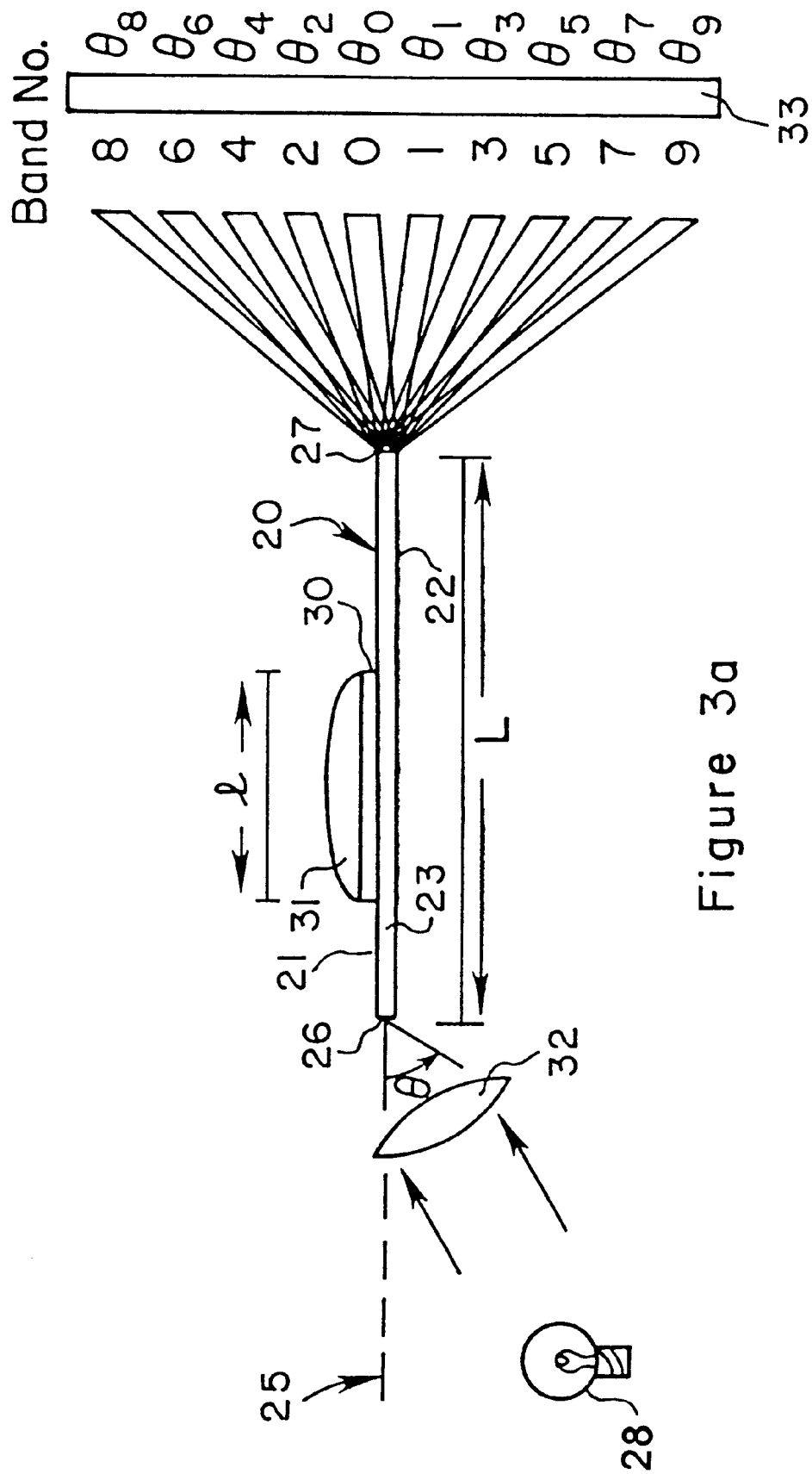
FIG. 3A is a schematic drawing of a lightpipe SPR sensor of this invention in which input light is end-coupled into the lightpipe at a range of angles below the axis of the lightpipe. Light exits the lightpipe in an angular array of bands alternating above and below the axis.
Figure 3B:
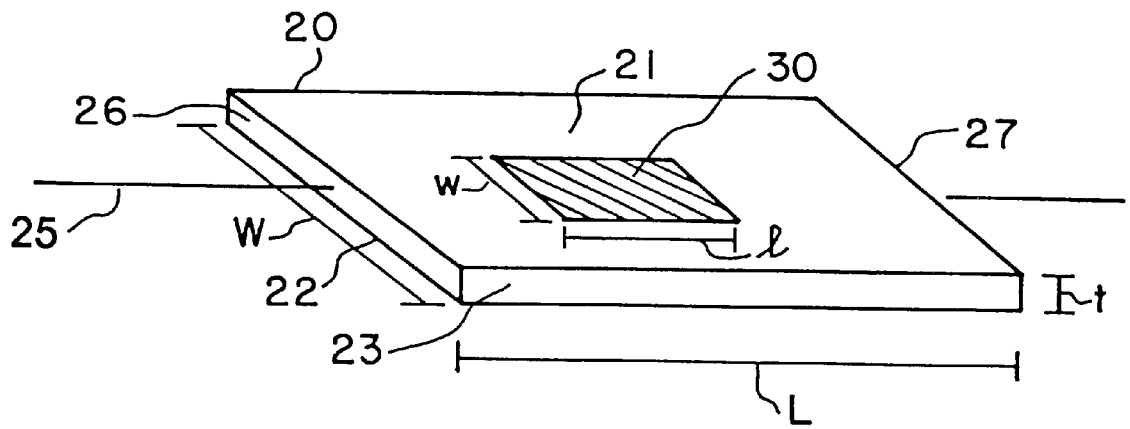
FIG. 3B is a perspective view of the lightpipe sensor of FIG. 3A showing the placement of the sensing region on the external top surface of the lightpipe.

A first order SPR planar lightpipe sensor configuration of this invention is illustrated in the side view of FIG. 3A and the perspective view of the lightpipe sensor of FIG. 3B. The sensor comprises a planar lightpipe (20) having top (21) and bottom (22) planar surfaces, sides (23) and input (26) and output (27) end faces. A lightpipe is fabricated from a dielectric substrate material that is substantially transparent to input light. For example, various types of glass and crystals, including sapphire, and various types of plastics and polymers can be employed as the lightpipe materials. The planar lightpipe can be a uniform slab of substrate with uniform length (L), width (W) and thickness(t) (as shown in FIG. 3B), where the length is defined as the dimension along which light traverses the lightpipe. Alternatively, the longitudinal input and output ends can be beveled. The lightpipe is preferably substantially longer than it is thick (L>>t). In the configuration of FIG. 3A, light is end-coupled into and out of the lightpipe. The longitudinal end faces (26 and 27) are polished at about 90° (substantially perpendicular to the planar top and bottom surfaces). The SPR sensing area (30) of the illustrated sensor is fabricated on one planar surface of the lightpipe, which is designated as the top surface in all configurations described herein. The sensing area of length (l) and width (w) is shown as placed centrally on the lightpipe surface in FIG. 3B. A sample cell (31) allows the sensing area to interface with a dielectric sample. Collimated white light, from light source (28) is asymmetrically coupled into the input end of the lightpipe, for example by focusing the light, through a cylindrical lens 32 at the input face at a range of angles ($\theta$) filling angles on only the lower side of the optical axis of the lightpipe (25). The input light must comprise TM polarized light, but the TE component of the light need not be removed. To reduce noise levels at the detector, it is preferred in all SPR configurations herein that the TE component of the light be substantially removed prior to light detection.

The sensing area comprises a SPR-conducting layer, and optionally comprises an adherence layer, a reactive layer, a dynamic range controlling layer or combinations thereof.

The term "lower side" is used in reference to the top and bottom lightpipe surfaces as defined above. The optical axis of the planar lightpipe extends the length of the lightpipe passing through the center of the input and output faces. That axis defines a plane cutting through the center of the lightpipe parallel to its top and bottom planar surfaces. The term "asymmetric light input" is used herein when light entering the lightpipe at a range of angles asymmetric with respect to that plane and consists of a range of angles either below that plane or above that plane, but not both. In contrast, as discussed below, "symmetrical light input" refers to light input that is symmetrical with respect to the axis plane with a range of angles both above and below the plane.

When the planar lightpipe is asymmetrically illuminated as illustrated in FIG. 3A, the output consists of discrete angular bands (b) (e.g., b=0–9 in FIG. 3A) (Smith, W. J. (1992), *Modern Optical Engineering. The Design of Optical Systems,* 2nd ed., (McGraw Hill), p. 192). As the propagation angle ($\theta_b$) increases down from the axis (corresponding to increasing band numbers in FIG. 3A), the direction of the output alternates in bands above or below the lightpipe axis. This is caused by the alternating number of reflections inside the lightpipe, with an odd number of reflections causing the rays to be directed down, and with an even number, directed up.

The light exiting the lightpipe of FIG. 3A can be imaged on an imaging screen (33) as shown. Other light detection schemes can be employed. For example, each angular band can be individually focused into a spectrograph to obtain the reflection spectrum as a function of wavelength. Each discrete angular output band contains a different white light SPR reflection spectrum that represents the average over a small range of angles, which is approximately equal to t/L radians.

Figure 3C:
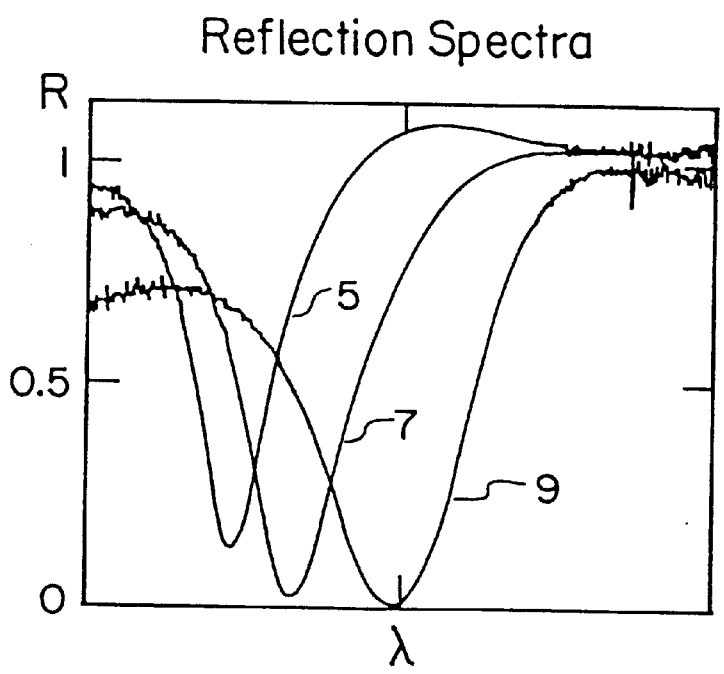
FIG. 3C provides the experimental reflection spectra for bands 5, 7 and 9 from the device of FIG. 3A where water is the sample.

FIG. 3C illustrates the reflection spectra with SPR feature for output bands 5, 7, and 9 from the SPR configuration of FIG. 3A obtained using a water sample. These spectra were obtained using a spherical lens to image each band into the input of a fiber optic spectrograph detector. The number of angular bands that can be collected and detected is dependent upon the specific optical system design.

Figure 4:
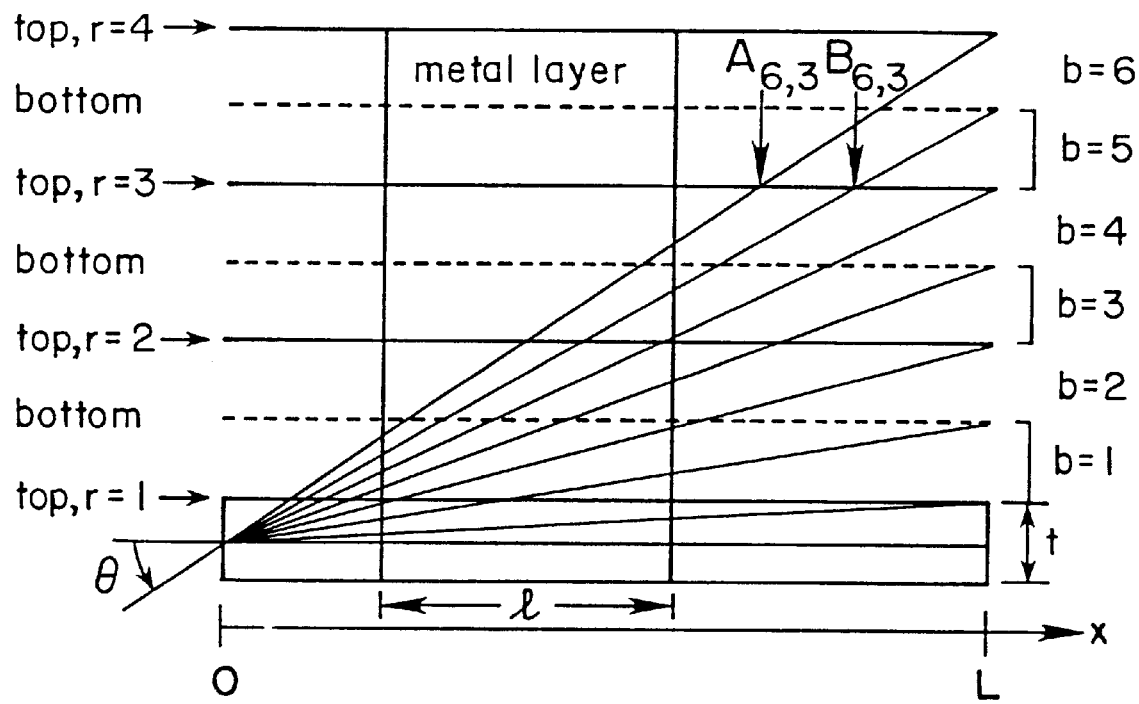
FIG. 4 is a drawing that illustrates unfolding a lightpipe multiple times with the straightened light rays passing through the virtual location of the top surface multiple times. $A_{b,r}$ refers to the $r^{th}$ top surface reflection location for maximum angle ray of the $b^{th}$ angular band and $B_{b,5}$ refers to the reflection location for the corresponding minimum angle ray.

In order to optimize the geometry of a lightpipe sensor and optimize the location of sensors on the lightpipe for a particular application, it is necessary to know the angular range of each band and the locations at which the band reflects off of the top surface (where the sensing layer will be positioned.) The angular extremes of each band can be calculated by "unfolding" the lightpipe multiple times as described in Smith, W. J. (1992), *Modern Optical Engineering. The Design of Optical Systems,* 2nd ed., (McGraw Hill), p. 192. When this is done, the light rays appear to straighten out, as shown in FIG. 4, and it can be seen that the different bands hit different locations along the length of the top surface, and that the extreme rays for each band are defined by the lines from the source spot to the top and bottom of the aperture formed by the virtual lightpipe end. For a point source located at the center of the input face, the steepest angle for a band "b" is given by:

$$\theta_{max_b} = \arctan\left(\frac{(b+0.5)t}{L}\right) \quad (4)$$

where t is the lightpipe thickness, L is the lightpipe length, and b is a positive integer which refers to the band number determined by the number of internal reflections. The shallowest angle in a band corresponds to the steepest angle in the previous band, ($\theta min_b = \theta max_{b-1}$). Therefore, the range of angles ($\Delta\theta = \theta max - \theta min$) subtending each band scales with t/L. For input white light, as $\Delta\theta$ is made smaller, by increasing L with respect to t, each band becomes more like a collimated white light beam, which has the effect of reducing the width of the resonant dip.

The same unfolded diagram can be used to find where each band interacts with the sensor area on the top surface. Referring again to FIG. 4, and assuming a point source located at the center of the input face, the location where a ray passes through a virtual surface corresponds to the location of a reflection off the top or bottom of the lightpipe. The location where the $b^{th}$ band makes its $r^{th}$ reflection off the top surface is calculated using the relationships for $A_{b,r}$ and $B_{b,r}$ in equations 5 and 6. At the point of reflection, the diverging band spreads across the top surface from $A_{b,r}$ to $B_{b,r}$, where $A_{b,r}$ is the horizontal distance from the input end to the reflection location for the steepest angle and $B_{b,r}$ is the distance for the shallowest angle.

$$A_{b,r} = \frac{(2r-1.5)L}{b-0.5} \quad (5)$$

$$B_{b,r} = \frac{(2r-1.5)L}{b+0.5} \quad (6)$$

If $A_{b,r} < x < B_{b,r}$ for any surface location x, then that location is illuminated by the $r^{th}$ reflection of the $b^{th}$ band. The location and size of the top surface reflections for the first 14 bands of a light pipe are shown as horizontal lines in FIG. 5. The horizontal axis indicates percent of the lightpipe length, and the vertical axis is the band number "b." The illuminated regions extend for the length of the horizontal line segments shown, whereas the width of the spot (w in FIG. 3B) depends on the width of the beam used in the experimental setup. For example, the incident light can be focused to a point on the input face or a line that extends across the input face of the lightpipe. In the equations above, the illumination locations for a given band are independent of the lightpipe thickness, and the length can be factored out to leave a fraction of the total length. Thus, the reflection pattern in FIG. 5 is independent of the light pipe dimensions.

Figure 5:
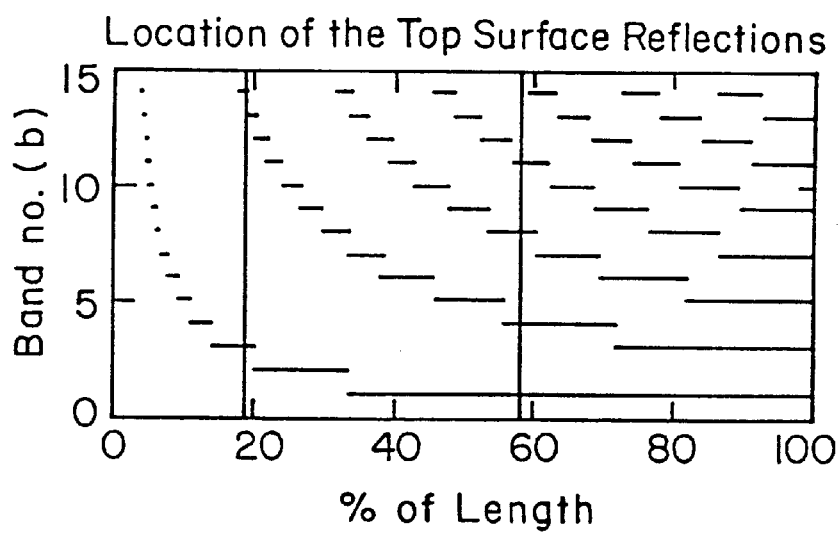
FIG. 5 is a graph of lightpipe top surface reflections (where the sensor is positioned) as a function of angular band number showing the location and size of illuminated spots on the top surface of the light pipe for each angular band as horizontal solid line segments. A reflection extends from the beginning to end of the line segments. The shaded area is the location of the SPR-supporting metal layer, i.e., the sensing area. Band numbers are as illustrated in FIG. 3A and as indicated in FIG. 4.

The pattern in FIG. 5 can be used to optimize the sensing area (conductor or metal layer) locations and size for a specific sensing application. Some first order sensing applications require obtaining resonances from a maximum number of bands. In such a case, a band with partial or multiple reflections off the sensing film would be acceptable as long as a resonance was observed. For example, in measuring the dispersive RI, it is preferable to analyze as many different bands as possible each having a different resonance at different wavelengths to allow determination of RI at many wavelengths. In another example, many different components of a given sample can be simultaneously assessed using differential functionalization of the SPR sensing areas (i.e.,providing different reactive layers) on a lightpipe sensor surface. In this case, each exiting angular band would carry information about a different component (analyte) in the sample. In yet another example, having the ability to analyze multiple bands sensing the same sample or analyte provides several benefits. It allows an internal confirmation or check of a given measurement, thus avoiding spurious readings that might occur on a single channel. Further, since the higher the band angle, the greater its sensitivity and the less its dynamic range, the availability of multiple bands allows a selection of the highest sensitivity channel for a given sample.

Other applications might require high sensitivity of $\Delta\lambda_{SPR}/\Delta RI$ in a limited number of bands. These applications would benefit by designing the sensor to operate at the highest angle possible, with only one or two reflections per band. For example, a bioassay for an analyte present at a very low concentration, where the dynamic range was known, preferably would be done employing a single band with as high a sensitivity as possible.

A large number of high angle bands are made available, for example, by placement of the SPR-sensing area within the first about 20% of the length of the lightpipe. In such a configuration, low angle bands will not hit the sensing area placed in this region. In addition, sensing area placements can be selected for interaction of a particular band with a particular sensing area. For example, a narrow sensing area located near the 50% L mark would be optimal for band 13, but adjacent bands would miss the sensing area.

In addition, the pattern in FIG. 5 can be used to position multiple sensing areas along the length of the lightpipe such that different bands of light will interact with different sensors. The individual sensing area can, for example, have different selectivity for interaction with species in the sample.

In order to maximize the number of useful bands, the optimization is an iterative process based on observing the pattern in FIG. 5, and positioning the sensing area so that it reflects as many bands as possible. In general, the region near the beginning of the lightpipe contains a reflection from most bands and has wide spacing between reflections. The positioning of sensing areas in this region requires looser fabrication tolerances. Experience has shown that bands must have at least one half of a reflection off the sensor to provide a useful resonance, and that three or more reflections off the sensing area tend to broaden the resonance and flatten its bottom, complicating the determination of $\lambda_{SPR}$. In the case of designing for the highest sensitivity, the first step is to calculate the total internal reflection (TIR) angle, $\theta_{critical}$ where:

$$\theta_{critical} = \arcsin\frac{n_{cladding}}{n_{substrate}} \quad (6)$$

where $n_{substrate}$ is the index of refraction of the lightpipe substrate and $n_{cladding}$ is the index of the medium in contact with the substrate surface at the reflection location, e.g., air or sample. The bands closest to the critical angle are then used. The wide spacing between reflections at the beginning of the lightpipe lends itself to selecting a sensing area where the first illuminated spot for each band is completely covered (in FIG. 5) with the proposed sensing area to provide a single, complete reflection.

Figure 6:
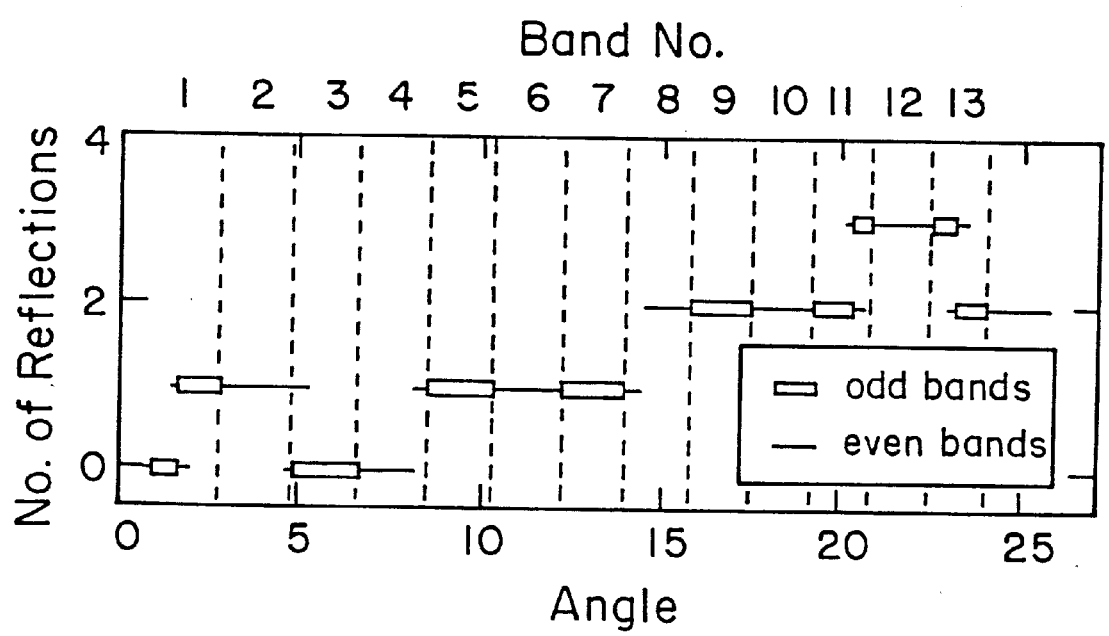
FIG. 6 is a graph of the results of calculations of the number of reflections for each light ray off the metal sensing surface of the lightpipe where the position of the sensing surface is as shown in FIG. 5. The calculation indicates that bands 5, 7, and 9 will experience 1, 1, and 2 reflections, respectively, while bands 1, 3, and 4 will all only experience partial reflections. The graph shows the range of angles of each band.

To compare theory with experiment, ray tracing was used to count the number of times each ray, as illustrated in FIGS. 4 and 5, was reflected from the sensing area of an experimental sensor of FIG. 3A (see Example 1). The graph in FIG. 6 shows the calculated number of reflections that a ray of given angle (by Band No., as illustrated in FIG. 3A) makes off of a sensing area located on the planar lightpipe surface as in FIG. 3A. In FIG. 6, rays contained in odd numbered bands are indicated with thick lines, while rays contained in even numbered bands are indicated with thin lines. The calculations based on ray theory in FIGS. 5 and 6 predict that band 3 will only have a partial reflection off the sensing area, almost missing the sensing area entirely, and that bands 5, 7 and 9 will respectively undergo 1, 1, and 2 complete reflections off the metal sensing area. The graph of FIG. 6 also indicates the range of angles in each band. A double reflection squares the reflection coefficient, causing the resonance to broaden out, and giving a broader dip in the spectral intensity. A resonance on band 3 could not be experimentally measured in the test sensor. As illustrated in the spectra of FIG. 3B, the resonance spectrum for band 9 is significantly broadened compared to the spectra for bands 5 and 7. The observed spectra confirm the model's prediction of the number of times each band hits the metal surface. However, the model is sensitive to the position at which light is focused on the input face. The model used assumes that the rays originate at the center of the input face of the lightpipe. It was found experimentally that when light is focused elsewhere on the input face, the angular content of each band shifts. For example, if the spot of focus moves from the center to the bottom on the input face, the angles in each band will shift over one half of a complete band worth of angles. A slit or aperture on or at the input face can constrain the input light to one location. These factors should be taken into consideration when using the model to position a sensor for a given application.

Figure 7:
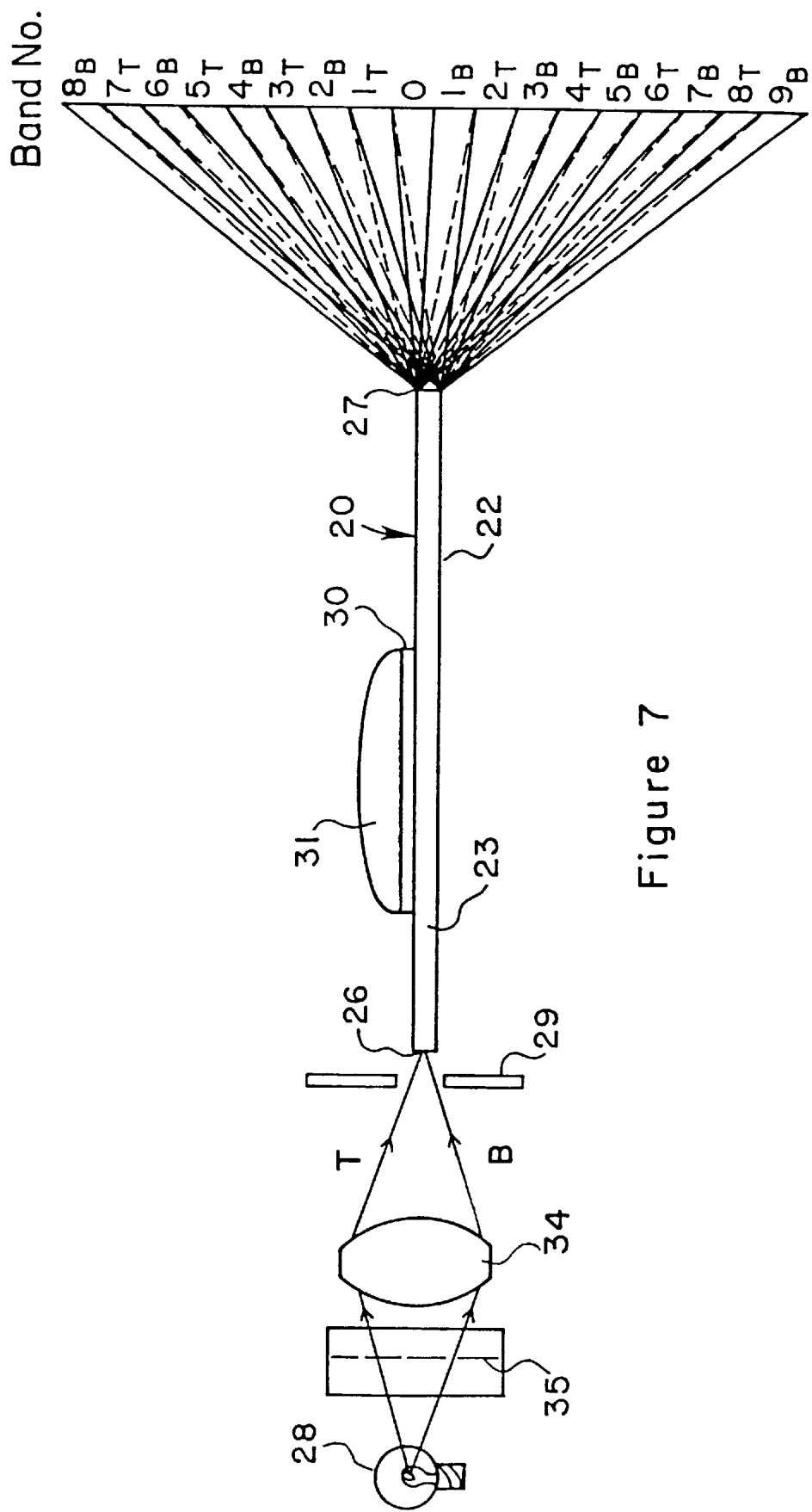
FIG. 7 is a schematic drawing of a planar lightpipe sensor of this invention in which light is end-coupled into the lightpipe by focusing light at the input face at a range of angles above and below the lightpipe axis (symmetrical light input). Input light filling angles above the axis exits the lightpipe in an angular array of bands alternating above and below the axis. This exit pattern is complementary to the exit pattern of bands from input light filling angles below the lightpipe axis.

If light is introduced into the lightpipe of FIG. 3A symmetrically at angles above and below the axis of the lightpipe, the light focused on the lightpipe input face from above the lightpipe axis will also give a pattern of angular bands on exiting the lightpipe. This lightpipe configuration is illustrated in FIG. 7 where a cone of angles of light is focused at input face 26. The cone is shown focused at the center of the input end face. The input optics of FIG. 7 include two cylindrical lens 34 and 35. Lens 35 collimates light across the width of the substrate and lens 34 focuses a range of angles relative to the substrate thickness on the input face. The configuration includes an aperture (29) to minimize input of undesired angles of light. The output angular bands are indicated and labeled by band number and T or B (e.g., 1T, 1B, etc.) to indicate that a band originated from input angles above (T) or below (B) the lightpipe axis. The banded output pattern from light of angles above the axis (1T, 2T, 3T, etc.) will be the complementary pattern of that from light focused at angles from below the axis (1B, 2B, 3B, etc.). If the lightpipe planar surfaces are perfectly flat and, if the exit end is polished perfectly flat, the complimentary pattern will fill the gaps between the light bands in the pattern generated by light focused from below the axis when viewed near the output face of the lightpipe.

If the lightpipe structure is not perfectly flat, the input end is not perfectly flat and/or the input light is not perfectly focused to a point, there will be some overlap of exiting bands (as indicated in the FIG. 7) in the symmetric light input configuration. The exit optics and detection scheme used must take into account potential overlap of the angular output bands. Each angular band can be individually focused into a fiber optic pickup for individual sequential analysis or two or more angular bands can be analyzed simultaneously with a multiple channel detector. The banded output pattern seen in side view in FIG. 7 is the result of the range of illumination angles provided by lens 34 and does not rely on whether the light is in fact collimated by lens 35.

Light input is shown in FIG. 3A as completely asymmetric (all angles below the axis) and in FIG. 7 as completely symmetric. Light can, of course, be introduced in a manner between these extremes. There is no requirement that the same range of angles above and below be introduced. The use of the asymmetric light input scheme illustrated in FIG. 3A avoids potential overlap of angular bands, simplifying output detection, and is in this sense preferred. However, if angles on both sides of the axis are filled, there are more output bands that are closer together, thus providing more choices for optimization.

The discussion and calculations illustrated above regarding optimized placement of the sensing area in the lightpipe assume asymmetric light input below the optical axis of the lightpipe and placement of the sensing area, by definition, on the top planar surface of the lightpipe. As noted above, the lightpipe sensor can be configured with symmetric light input (FIG. 7). The lightpipe sensor can be also be configured with asymmetric light from the top side of the lightpipe, i.e. light input filling angles above the lightpipe axis, with the sensing area still located on the top surface of the lightpipe. Optimization of placement of the sensing area in these cases is done using procedures and calculations analogous to those discussed above.

The lightpipe of FIG. 3A is shown with both input and output ends perpendicular to the top and bottom surfaces. Both the input and output ends of the lightpipe can be beveled, i.e., angled with respect to the top and bottom surface. FIG. 3A shows asymmetric light input of a wedge of angles from below the axis. FIG. 7 below shows input of a cone of light on a perpendicular input face.) Light can be coupled into the lightpipe at a range of angles by focusing a cone or wedge of light (as in FIGS. 3A and 7) at the beveled or angled input face. Those of ordinary skill in the art will appreciate that an input configuration equivalent to the input configuration of FIG. 3A can be achieved by directing the wedge of light along the optic axis of the lightpipe and focusing the light at a beveled edge, i.e., the equivalent of off axis input can be achieved with on axis input to a beveled end. The input face can be beveled so that it makes either an acute or an obtuse angel with the bottom planar surface of the lightpipe. The choice of bevel angle in on-axis light input allows a selection of a range of input angles both above, or below (or both above and below) the axis.

Figure 8:
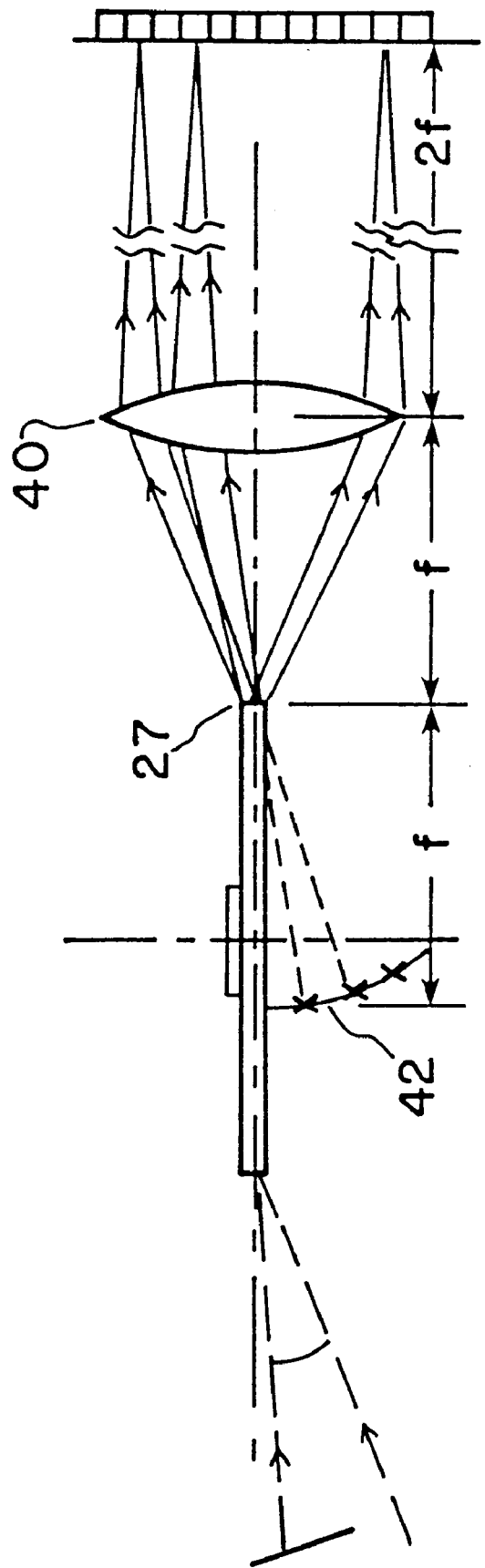
FIG. 8 illustrates an alternate configuration of the asymmetric input SPR sensor of FIG. 3A wherein the exit optics of the lightpipe employ a telecentric lens to redirect and focus angular output bands.

One particularly useful means for collecting the output light of the lightpipe is illustrated in FIG. 8. In this side view, an SPR sensor of FIG. 3A incorporates a telecentric system wherein cylindrical lens 40 is placed at about one focal length from the output end (27) of the lightpipe. In this configuration lens 40 is a telecentric lens and the lightpipe output end (27) is a telecentric stop. The lens collects light exiting the lightpipe and focuses it into the detection optics (Smith, W. J. (1990) *Modern Optical Engineering. The Design of Optical Systems,* 2nd ed., McGraw Hill, N.Y.).

A telecentric system comprises a telecentric lens which may itself have several components. A telecentric lens is a lens in which an aperture stop (the telecentric stop) is located at the front focus and results in the chief rays of light passing through the lens being substantially parallel to the optic axis of the lens in image space. In the illustrated telecentric system, a cylindrical lens simultaneously redirects and focuses output bands onto a plane perpendicular to the lens axis and makes the bands substantially parallel to the optical axis of the lens. A spherical lens placed in an analogous telecentric structure (i.e., a spherical telecentric lens) simultaneously redirects and focuses the light from the bands (as would be seen from both the side and top views of the substrate, not shown). A telecentric lens images output bands into individual spots or lines, so that a detection device, e.g., fiber optic pickup, photodetector or entrance slit for a spectrograph, can be placed at the image location (about 2 focal lengths from the telecentric lens, 2f) to capture the signal with minimal effects from defocus. The telecentric lens is positioned one focal length from the output end of the lightpipe sensor so that the output face of the sensor acts as a telecentric stop (41). Alternatively, albeit with significant light loss, a separate output aperture can be provided to reduce the angular width of each band. Since each band of light passes through an aperture at the focus of the lens, the path of each output band is straightened out to be substantially parallel to the optical axis of the lens.

The individual bands exiting the lightpipe can be considered to originate from locations along a virtual arc (42), so that each band will come to a focus some distance behind (2f) the telecentric lens. When the telecentric lens has a focal length approximately equal to the distance between the virtual source origin to the end of the lightpipe, the size of the output focus and spot will be comparable to the size of the incident spot. This choice of focal length for the lens is preferred for efficient light collection by the detection optics.

The telecentric lens is preferably chosen so that the field curvature of the lens is matched to the profile of the virtual arc of sources (Smith, W. J. (1990) supra and Optics Guide 5, Melles Griot Catalog (1990)). When the condition is met, all the bands will focus at a common plane perpendicular to the optical axis as shown in FIG. 8. This choice of lens is particularly useful and preferred for capturing multiple bands of light at the same time. It is also preferred when capturing multiple bands that the lens is chosen and positioned so that the separation between the center of each band is constant. Then the focus of the light into the detector optics can be adjusted by moving the structure (sensor and lens) along the axis without the need for transverse adjustment.

In FIG. 8, the optical axis of the telecentric lens is aligned with the optic axis of the lightpipe. The lens can be employed in other output optical geometries for capture of angular bands. For example, the telecentric lens axis can be aligned with the center ray of any angular output band to capture adjacent bands. In this case, the telecentric lens will redirect and focus the bands passing through it to make them substantially parallel to the optical axis of the lens (i.e., parallel to the direction of the output band to which the lens is aligned).

The output optics of the lightpipe of FIGS. 3A, 7 and 8 preferably include a means for correcting for spherical and chromatic aberrations so that a good image of the source corresponding to each angular band can be formed. This type of correction can be accomplished for example using a field flattener.

Since it is possible to calculate the precise range of angles in each band of light (exiting the lightpipe or propagating through the lightpipe), the lightpipe sensor of FIG. 3A in which the sensing area consists of an SPR- supporting conductor layer, specifically an SPR-supporting metal layer, of known thickness can be calibrated using a model matching technique. By measuring the length and thickness of the lightpipe with a micrometer, the angles of each band can be calculated with high precision. If the thickness of the metal sensing layer is accurately known, a Fresnel reflection model can be used to find the RI which would excite SPR at the measured resonance angle. If the metal thickness measurement is not accurate, metal thickness in the model can be corrected by using a liquid standard whose RI is measured on an Abbe refractometer or by other appropriate methods. Metal thickness can be adjusted in the model until the modeled resonance at the wavelength at which the standard is measured matches the experimental resonance of the liquid standard.

Figure 9A:
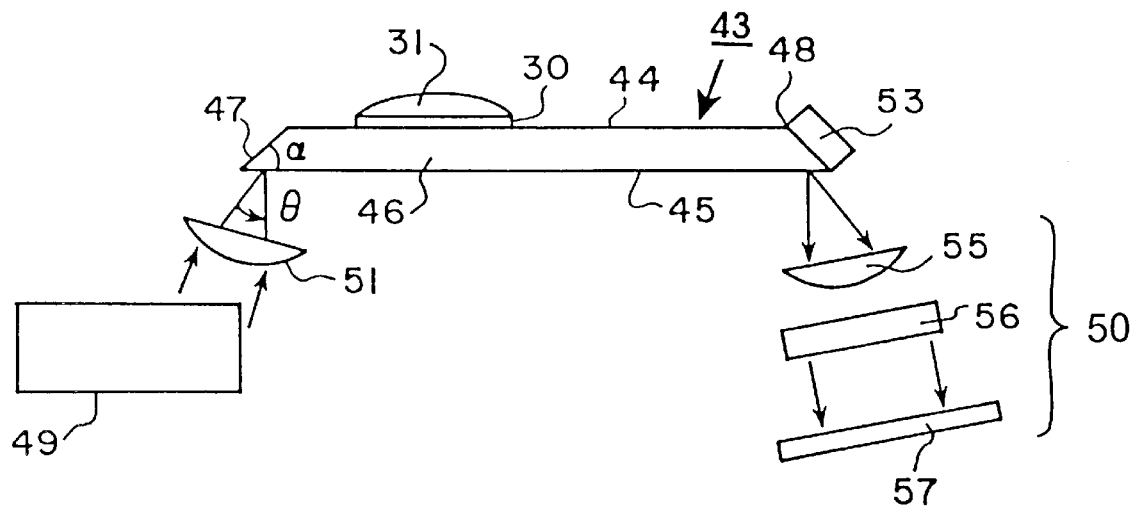
FIG. 9A illustrates an alternative first order SPR sensor configuration with light input into the lightpipe through the lower planar surface and off a mirrored bevel on the input end of the lightpipe. Light exits the lightpipe through a built-in diffraction grating on a beveled out put end of the lightpipe.

An alternative first-order planar lightpipe sensor configuration is illustrated in FIG. 9A. As in the sensor of FIG. 3A, the planar lightpipe (43) has a top (44) and bottom (45) surface, sides (46) and input (47) and output (48) ends. In the illustrated configuration, the input and output ends are symmetrically beveled at a selected angle $\alpha$ to the bottom surface by polishing. In a specific embodiment the input and output bevels are each at a 45° angle to the bottom surface of the lightpipe. Again in the illustrated configuration, the upper planar face of the sensor carries the sensing area (30) in which SPR can be excited and which contacts the dielectric sample in a sample cell (31). The sensing area comprises an SPR-conducting layer and optionally comprises an adherence layer, a reactive layer, or a dynamic range-controlling layer. Light from a white light source 49, and which is optionally passed through a TM polarizer, enters and exits the lightpipe at its input and output ends, respectively, through the bottom planar face of the lightpipe. In this configuration the light source and detector system (50) are positioned away from the sample so that the chemistry and optics can be separated. Collimated white light is focused to a point by a spherical focusing lens (51) (or a line using a cylindrical lens) at the bottom surface of the lightpipe near its input end with a range of angles $\theta$ with respect to the bottom of the light pipe. The light is focused such that it reflects off the bevel of the input face while stray light is directed away from the detector. The bevel is illustrated as about 45° but can be any angle that will allow light coupling into the lightpipe. The bevel can be metalized to act as a mirror or it can allow light to couple into the lightpipe via total internal reflection (TIR) off its surface. The light entering the lightpipe in such a configuration need not be and is preferably not perpendicular to the bottom surface of the lightpipe. The range of input angles of light is limited by TIR inside the lightpipe.

The output bevel (also shown as 45° with respect to the bottom surface in the figure) directs the light down towards the input side of the sensor into a detector system 50. A diffraction grating (53) index matched onto the output bevel reflects light out of the lightpipe through the bottom surface. The grating is oriented to disperse each band out of the page and a portion of the dispersed bands are collimated with cylindrical lens (55) and imaged with cylindrical lens (56) onto an output detector plane for detection, for example by an imaging detector (57) to produce an image of reflected light intensity vs. angle and wavelength. Alternatively, a diffraction grating can be formed directly on the beveled output end so that no index matching is necessary. Further, the diffraction grating can be replaced with a mirrored surface, e.g., the a mirror can be deposited on the beveled end.

Figure 9B:
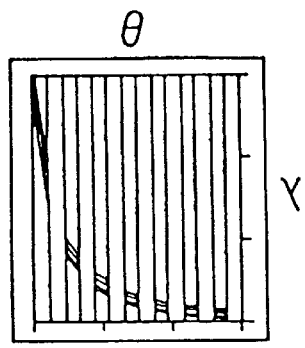
FIG. 9B illustrates an idealized contour plot detected at the output plane by an image detector of the SPR sensor of FIG. 9A of the reflection coefficient of the output light as a function of both wavelength and angle.
Figure 10:
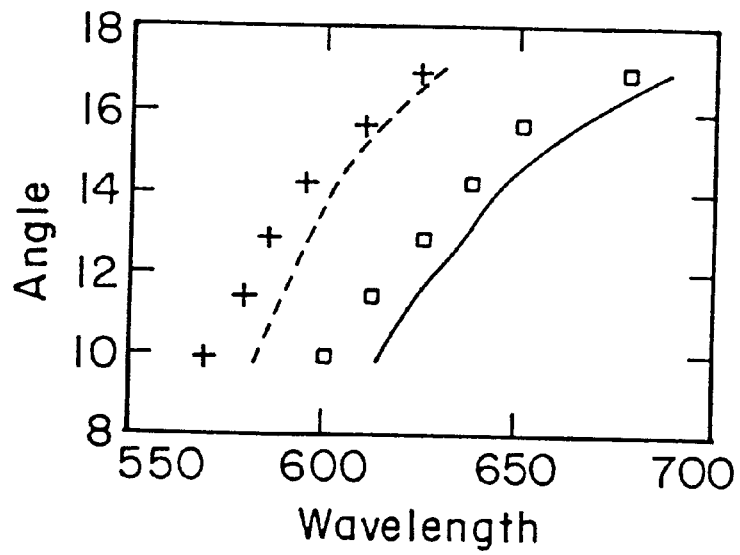
FIG. 10 compares theoretical values of the SP resonance wavelength ($\lambda_{SPR}$) and experimental measurements of $\lambda_{spr}$ determined using a sensor of FIG. 9A. $\lambda_{spr}$ is plotted as a function of the center angle for each angular band for samples of acetone and water.

The inset graph of FIG. 9B illustrates an idealized contour plot of reflection coefficient of the output light as a function of both wavelength and angle. Cylindrical lens (55) is positioned to affect only those bands exiting the lightpipe that have undergone an odd number of reflections. The complementary pattern produced by the even bands is missed by lens (55). The output spectra can be analyzed to determine $\lambda_{SPR}$ for each band. The measured center angles of each band are plotted against $\lambda_{spr}$ in FIG. 10 and compared to values calculated using a model discussed in Example 3. FIG. 10 shows that $\Delta\lambda_{spr}/\Delta RI$ measured using the sensor closely matched values predicted by theory.

Figure 11:
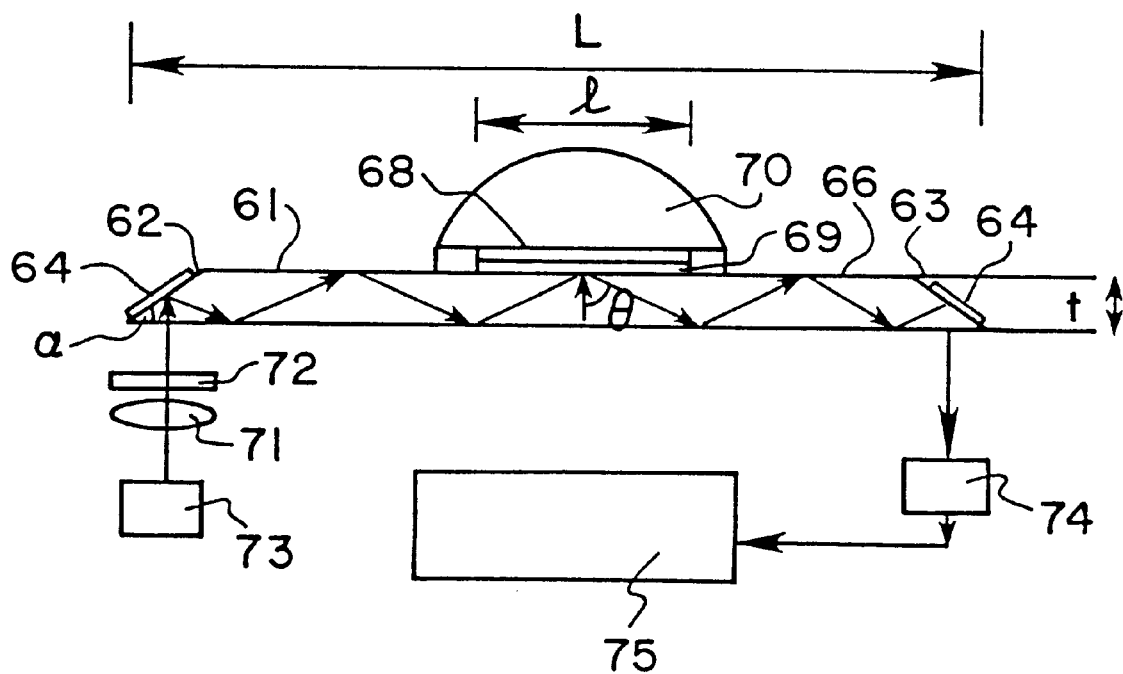
FIG. 11 illustrates a particular embodiment of a planar lightpipe zero-order SPR sensor configuration particularly useful for single-angle light input. The length of the lightpipe (L), the width of the sensing area (W) and the bevel angle $\alpha$ are selected to maximize RI sensitivity.
Figures 12A, 12B, 12C, 12D:
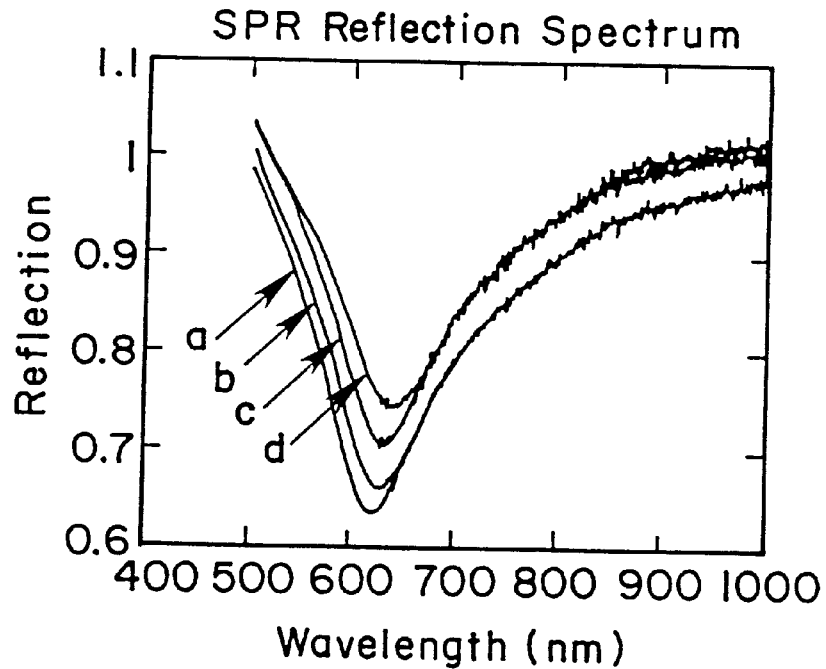
FIGS. 12(a)–12(d) are SPR refection spectra measured with the single-angle SPR lightpipe sensor of FIG. 11 for aqueous glycerol solutions of concentrations (weight percent of solution) of (a) 4.02%, (b) 6.22%, (c) 7.30%, (d) 9.50%.

A specific embodiment of the planar lightpipe single-angle SPR sensor of this invention is illustrated in FIG. 11. FIG. 11 gives a side view of the lightpipe with optical component for light input and detection. In this zero-order sensor, the planar lightpipe 61 of length, L, and thickness, t, where L is the length of the longer of the top or bottom surface, is beveled at a selected angle α at both its input (62) and output (63) end. Both beveled surfaces can be mirrored (64). The lightpipe has a top planar surface (66) carrying an SPR sensing area (68) comprising an SPR supporting-conducting layer (69). The sensing area optionally comprises an adherence layer, between the lightpipe surface and the conducting layer and optionally comprises chemically or biochemically selective overlayers, reactive layers, which can provide for selective adherence of analytes from the sample. In addition, the sensing area optionally comprises dynamic range-controlling layers, and passivation or protective layers. The sensing area of length (l) is symmetrically positioned along the length (L) of the lightpipe. The sensing area can extend over the entire width of the lightpipe or over a portion of that width. In the sensing configuration, the sensing area is in contact with a dielectric liquid or gas sample, for example in a static cell (70) or flow cell configuration (not shown).

A collimated beam of white light comprising TM polarized light (preferably TM polarized light) is coupled into the lightpipe through the bottom planar surface and reflected from the internal surface of the input bevel. As illustrated, light propagates through the lightpipe by TIR to hit the sensing area at a single fixed angle, θ, which is 2α, and excite SPR at the sensing area. Since light cannot in a practical sense be perfectly collimated, the light hitting the sensing area comprises a small range of angles dependent on the quality of input collimation. The output bevel is symmetrical to the input bevel and couples light downward out of the lightpipe. This lightpipe structure was designed to be symmetrical so that metal sensing layer is located in the center of the top surface. The bevel angles (α) were chosen so that the incident angle of illumination on the active sensing layer (θ=2α) would be high enough to ensure good sensitivity. The angle that ensures good sensitivity depends on the substrate used and the particular application. For glass and low concentration aqueous samples, 22°–25° or 75°–78° from the normal is a good balance between high sensitivity and the resonance occurring past the wavelength range of a silicon detector.

The sensor of FIG. 11 comprises a non-monochromatic source, preferably a broad band or white light source. Light exiting the source (73) is collimated using collimator (71) and is optionally TM polarized using polarizer (72). The light may be collimated as a narrow beam that lands on a point on the center of the face of the input bevel. Alternatively, the collimated beam of light can be expanded in one direction using anamorphic optics so that it forms a collimated line across the width of the input bevel face. Collimated light enters the lightpipe, reflects down the lightpipe interacting with the sensing area, exits the lightpipe by the output bevel and is collected by output signal collector (74) (a collimator lens used backwards to image the collimated light into the fiber optic pick up of a spectrograph). The collected output then passes to a suitable detector (75) to measure reflected light intensity as a function of wavelength, e.g., a spectrograph.

Assuming a symmetrical lightpipe profile to position the sensing area in the middle along the length of the lightpipe, the length (L) of the lightpipe is chosen using equation:

$$L = t\cot(\alpha) + t\tan(2\alpha) + 2(2n+1)t\tan(2\alpha) \quad (7)$$

where n is an integer related to the number of reflections inside the lightpipe and t is the thickness of the lightpipe. The length (l) of the metal sensing layer is preferably selected so that light hits the sensing layer only once. The preferred maximum width $l_{max}$ of the sensing area to meet this condition depends upon t and α and is given by:

$$l_{max} = 2t\tan(2\alpha) \quad (8)$$

Exemplary reflection spectra obtained with the SPR sensor of FIG. 11 are provided in FIGS. 12(a)–12(d). See Example 3 for details of the measurements with the sensor of FIG. 11.

In alternative embodiments, diffraction gratings fabricated on the planar lightpipe can be employed at the input and output ends of the SPR lightpipe sensors to couple incident monochromatic light into or reflected monochromatic light out of the lightpipe. A diffraction grating can be introduced onto the bottom or top surface of the lightpipe near either the input or output end, or at both ends. The grating is created in or on the substrate material of the lightpipe by conventional methods, for example lithography and etching techniques standard in the semiconductor industry. Light is coupled into the lightpipe at desired transmission angles by focusing light at the appropriate incidence angles onto the input grating.

The SPR sensor planar lightpipes of this invention comprise a sensing area adhered to the external top surface of the lightpipe. Detection of a sample or a given species in a sample by the lightpipe SPR sensor is made, in part, by contacting the sensing area of the lightpipe with the sample. The sensing area is prepared by adherence of an SPR-supporting conductive layer to a selected area on an external longitudinal surface of the lightpipe. The position and length of the sensing area is selected to optimize the sensor for a given application.

The lightpipes of the SPR sensors of this invention are fabricated from a material that is transparent or semi-transparent to the range of wavelengths of light to be employed in a given application. Useful substrates include glasses, crystals, plastics and polymers. To insure TIR in the lightpipe, e.g., along the length of the lightpipe, the lightpipe is optionally provided with a cladding layer having an index of refraction different from that of the lightpipe substrate. The cladding is provided over the entire lightpipe (except for sensing area) or over selected portions of the lightpipe. Those of ordinary skill in the art know and understand how to select and can readily select a lightpipe substrate appropriate for a given application. Those of ordinary skill in the art also know how to select and can readily select an appropriate cladding layer for a given application and substrate material.

The sensing area comprises one or more layers which together support SPR. The sensing area comprises an SPR-supporting conductive layer. This layer may be a conductor, e.g., a metal layer that supports SPR or a semiconductor layer that supports SPR. Semiconductors useful in the conductive layer include silicon and germanium. Alternatively, conductive polymers can be used in the conductive layer.

The conductive layer can be a "SPR-supporting metal layer" which is herein means a highly-reflective metal that supports SPR at the metal/sample interface and has a permittivity constant wherein the real part of the permittivity is negative and its magnitude is greater than the magnitude of the imaginary part. For wavelengths in the visible and near-infrared (i.e., 400 nm–1000 nm), both silver and gold satisfy this criterion. The SPR supporting metal can also be a mixture of one or more metals or be composed of sequential layers of different metals. If the wavelength range utilized extends into the infrared, other metals, such as aluminum, copper and tantalum, may also be used.

Preferably the SPR-supporting conductive layer, e.g., the metal layer, is adhered to the lightpipe surface to a thickness which will optimize the measured resonance curve, i.e., to a thickness which makes the SPR resonance spectrum both deep and sharp, between about 400 Å to 700 Å thick. When the SPR-supporting metal layer is made of silver, the layer thickness preferably is between about 500 Å to 550 Å thick. Layers of silver thinner than about 400 Å result in substantially shallow and broadened resonances, and layers thicker than about 600 Å will result in significant diminishment or disappearance of the resonance feature. The range of thicknesses for gold SPR-supporting layers are also 400–700 Å, preferably 500–600 Å. Gold is preferred because of its inertness and resistance to oxidation. SPR-supporting metal layers can be prepared with sequential layers of different metals, for example, a base layer of silver combined with an upper layer of the gold for a total double layer thickness of between about 400 Å to about 700 Å. One of ordinary skill in the art can readily determine the appropriate thickness of the SPR supporting metal layer for a given lightpipe sensor application by varying the metal layer thickness to optimize the resonance curve.

SPR-supporting conductive layers are adhered to the lightpipe surface by methods known in the art. An SPR supporting metal layer can be adhered by standard procedures, including vacuum deposition, electron beam deposition, sputtering, chemical vapor deposition and the like. Layer thickness is controlled by well-known methods, for example employing a quartz crystal oscillator or other suitable thickness monitor. U.S. Pat. Nos. 4,997,278, 5,064,619, 5,351,127, and 5,485,277, for example, disclose, reference or summarize methods for adherence of an SPR-supporting metal layer.

Prior to adherence or deposition of the conducting layer a base or adherence layer is optionally applied to the substrate (here, lightpipe) surface. The adherence layer is typically a metal layer, such as chromium, nickel, platinum or titanium, less than about 50 Å thick, and more preferably about 20 Å thick.

The sensing area optionally contains one or more additional layers adhered to the SPR supporting conductive layer to yield a change in the effective refractive indices detectable by the sensor. Such additional layers can include a dynamic range-controlling layer, a reactive layer, a protective overlayer or any combination thereof. A variety of techniques are known and available to those in the art to provide dynamic range-controlling layers, reactive layers and protective layers in an SPR sensing area.

A "dynamic range-controlling layer" is a layer adhered to the SPR supporting conductive layer to alter the dynamic range of the SPR sensor. This layer has an index of refraction different (either higher or lower) than that of the SPR-supporting layer. For example, adherence of a layer of higher refractive index to the index of the substrate will extend the dynamic range of the sensor to include lower RI values. For example, U.S. Pat. No. 5,327,225, describes the use of an overlayer of relatively high refractive index material, specifically SiO, on a fiber SPR sensor with a silver SPR-supporting layer to shift the dynamic range of the sensor to a lower RI value.

A "reactive layer" is an optional layer in the sensing area which interacts with a sample or an analyte species in the sample such that the effective refractive index detected by the sensor is altered. The addition of the reactive layer permits the manufacture of an SPR sensor which is more sensitive or selective for a sample (or analyte in a sample). Suitable reactive layers include those used in biological sensors, e.g., an antigen, antibody, nucleic acid or protein bound to the SPR supporting metal layer. This type of reactive layer will selectively bind a species in the sample, for example, a cognate antibody or antigen or complementary nucleic acid in the sample, increasing the thickness of the reactive layer and causing a shift in the effective refractive index measured by the sensor. Most generally, suitable reactive layers are altered in some way by contact with the sample so that the effective refractive index as measured by the sensor is changed. Reactive layers also include sol-gel films and polymer coatings. Reactive layers can be adhered to the SPR-supporting conductive layer or to an overlayer on the conducting layer. The reactive layer should interface with the sample solution.

U.S. Pat. Nos. 5,055,265 and 5,478,755 relate to SPR sensor configurations utilizing so-called "long-range SPR" (LRSPR). LRSPR differs from traditional SPR in the use of a distinct layering in the SPR sensing area. LRSPR employs a thinner conducting layer (100–200 Å) than in traditional SPR (500–600 Å). An LRSPR sensing area is fabricated by first depositing a thin dielectric layer on the transparent substrate after which the thin conducting layer is deposited.

The metal layer can directly contact the dielectric sample, or a reactive layer can be laid down upon the conductive layer. LRSPR in general provides increased sensitivity. The sensor configurations of this invention can be employed for LRSPR by appropriate adjustment of the layers of the sensing areas.

Printz, M. et al. (1993) *J. Modern Optics* 40 (11):2095–2104 and Bussjager, R. and Macloud, H. (1995) *J. Modern Optics* 42(7):1355–1360 have described a variation of SPR that is designated "inverted SPR". These references are incorporated by reference herein for their description of "inverted SPR." This method differs from traditional SPR in that the SPR-sensing layer comprises a thicker layer (about 100 Å) of a metal, like chromium, which is usually used in an adherence layer, with a thinner layer of gold or silver (about 400 Å) on top (i.e., for contact with dielectric samples). The SPR signal has an inverted feature in it and the wavelength of the resonance for a given sample is shifted from that measured by SPR. The sensor configurations of this invention can be employed for LRSPR by appropriate adjustment of the layers of the sensing areas.

A number of methods have been described, are known and available to those of ordinary skill in the art, for the formation of reactive layers with sensitivity to a variety of biological or chemical species. Formation of the reactive layer on a metal layer may require an intermediate thin layer of material to passivate the metal or protect ligands in the reactive layer from reaction with the metal; For example, U.S. Pat. Nos. 4,844,613, 5,327,225, 5,485,277, and 5,492, 840 disclose or summarize methods for preparation of such reactive layers in SPR sensors.

An SPR sensor of this invention can be configured with one or more sensing areas. One or more active sensing areas (those capable of detecting changes in RI of a sample) and one or more reference sensing areas can be provided in an SPR sensor. Active sensing areas in an SPR sensor can be provided with different reactive layers (e.g., can be functionalized for interaction with different biological or chemical species or functionalized differently for interaction with the same biological or chemical species), different over- or underlayers, different dynamic range-controlling layers and/ or combinations thereof.

A sensing area on a planar lightpipe of this invention can, for example, be subdivided into lateral regions across its width to provide separate sensing channels, including reference channels and sensing channels with different analyte selectivities. Differential sensitivity can be provided by use of different reactive layers. One of the lateral regions of the lightpipe can function as a reference for other activated and functionalized sensor channels. If the reference region is not functionalized or activated (i.e., no reactive layer provided) it will serve to track temperature changes, variations in the light source and signal due to nonspecific adsorption of the analyte. Alternatively, the reference area can be coated with a thick layer of a reference material (a dielectric) so that it does not react to the sample and will serve to track temperature changes or variation in the light source.

A sensing area or a portion of sensing area can also comprise an overlayer that protects or insulates the SPR-supporting layer from changes in the RI of the sample. For example, a reference sensing area can be made by providing a sufficiently thick overlayer of a dielectric material, such as a cured epoxy on the SPR-supporting layer. The reference sensing area then senses, and be used to correct for, temperature variations, light source variations and related instrumental variations.

In practice, the refractive index along the sensing interface in an SPR sensor is temperature dependent, as are the characteristics of the light source and the detector in the sensor system. Temperature fluctuations lead to variation in the SPR excitation condition and cause undesirable shifts in SPR wavelength. Thus, temperature compensation of the SPR sensor can significantly improve the accuracy of sensor measurements. One way to deal with temperature variation is provide a means for keeping the sensor at a constant known temperature (e.g., temperature control). This may not be practical in certain sensor applications. Alternatively, a sensor can be temperature compensated by developing a complex algorithm to allow correction of sensors measurements as a function of temperature variations. A third method for accounting for temperature variations to improve sensor accuracy is to incorporate a reference SPR signal as the compensation mechanism. SPR sensor configurations employing the planar lightpipe of this invention are readily adapted to include multiple sensor channels, one of which can be employed as a reference for temperature compensation.

FIG. 14A is a side view of a planar lightpipe employed in SPR sensors of this invention. FIG. 14B is a top view of the sensor of FIG. 14A showing that the sensing area on the top surface of the planar lightpipe is divided into two parts along the width of the top surface, which constitute two different sensor channels (81 and 82). Both channels are fabricated on the same sensor substrate, for example on a standard microscope slide, and have an identical SPR- supporting conductor layer and optional adherence layer. The length and positioning of the sensing areas are selected as discussed above. Only one of the channels is active for sensing particular species in the sample solution. The sensing areas differ in the functionalization of the conducting surface for interaction with specific species in the sample. For example, only one of the sensing areas (81) contains a reactive layer, as described above, which interacts with a specific species in solution causing a shift in SPR resonance. The other sensing area, the reference sensor channel (82), is inactive to such interactions and SPR on this sensor channel is a function both of the effective RI of the sample and non-specific absorption events.

The configuration of FIGS. 14A and 14B is similar to that of FIG. 7. The optional aperture 83 has been adapted for use with two sensing areas. This configuration is illustrated with a flow cell 85. The detection optics include a cylindrical lenses, like 86 to collimate bands and spherical lens 87(*a, b*) to image bands into fiber pick ups (88*a,b*). As illustrated, the detection optics can be configured to conduct individual bands into individual fiber pick ups which ultimately lead to a detector. For example, an array of fiber optic pick ups can be provided to detect a plurality of angular bands, or one (or several) fiber optic pick ups which can be adjusted to pick up any desired angular bands can be provided.

As long as the functionalized (reactive) layer in the active layer is thin (generally these layers are only a few monolayers thick), the temperature dependence of the two channels is substantially the same. In the configuration of FIG. 14B the SPR channels share the same light source and detector system. Subtraction of the SPR signals (the reference SPR from the active sensor) yields the temperature independent system response to the interactive species. This referencing mechanism also removes the effects of light source fluctuations and system losses.

In an alternative multi-channel sensor, the reference sensing area and any active sensing areas are formed with the identical SPR-supporting conducting layer and the same adherence layer (if any). An overlayer is then applied to the reference sensing area to provide interaction with a layer of constant RI. For example, a relatively thick layer of cured epoxy can be used to overlay the SPR-supporting layer. The reference sensing area in this case does not respond to changes in sample RI or to any specific binding of analytes that might occur on the active sensing area(s) of the sensor. The reference sensing area responds to changes in temperature, light source and other possible instrumental variations.

In a multi-channel lightpipe sensor, the SPR signals from each channel can be independently collected and measured. For example, SPR signals from two adjacent channels shown in FIG. 14B can be collected using fiber couplers (88a and 88b) into adjacent fibers and then transmitted into the same spectrograph, one at a time, periodically through a fiber switch under time control. Switching time and spectrograph analysis in such a system can be synchronized by a computer. Alternatively, a two-channel (or multiple channel) spectrograph can be utilized. The on-site and real time temperature information of the whole sensor system, thus, can be collected for the reference signal and extracted from the active SPR signal by conventional signal processing methods.

Figure 15:
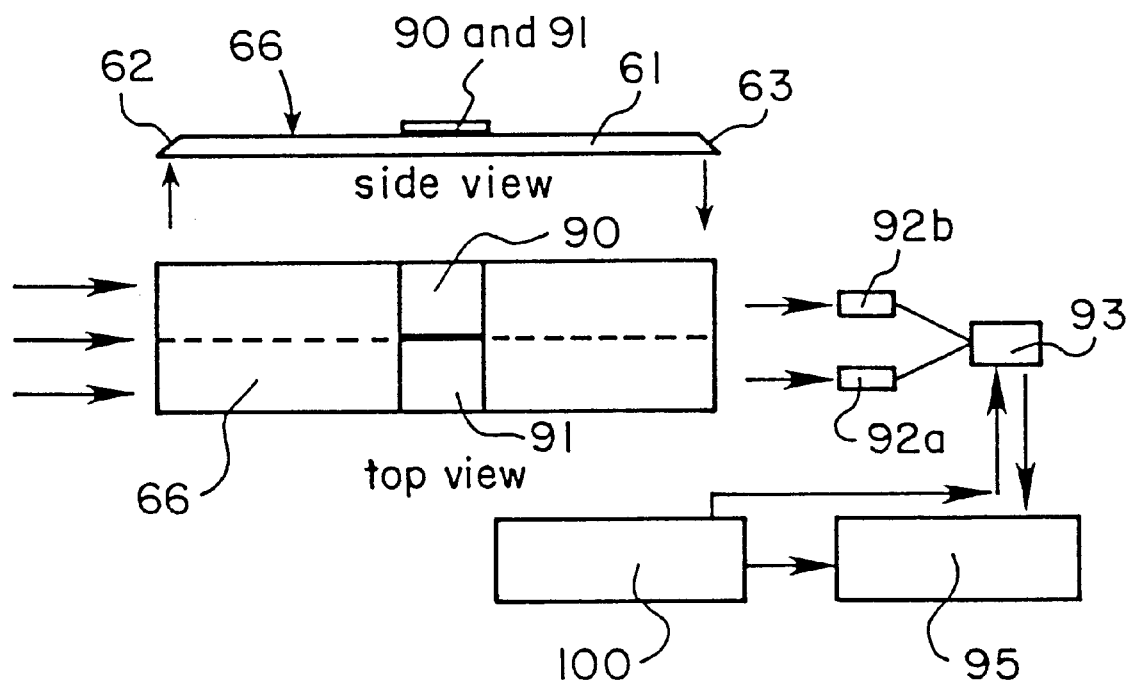
FIG. 15 is a drawing of a dual-channel configuration of the SPR lightpipe sensor of FIG. 11.

The beveled-ended zero order configuration of FIG. 11 is illustrated in FIG. 15 as a dual channel lightpipe sensor. A planar lightpipe was divided lengthwise into two sensor channels (90 and 91) adjacent to each other as shown in FIG. 15. Output from the two different sensing channels, at different positions along the width of the lightpipe, exits the lightpipe at corresponding positions along the width of the lightpipe and is separately collected by fiber couplers (92a and 92b), passed through fiber switch 93 and analyzed in a detector system comprising a spectrograph (95) under computer (100) control. The details of this configuration are discussed in Example 4.

Referring back to FIG. 6, there are specific reflection locations along the length of the top surface (as well as the bottom surface, but not shown) of the lightpipe unique to a given angular band and not shared by any other band. Therefore, individual angular bands can be used to monitor SPR on different locations along the length of the lightpipe surface. Different samples can thus be placed to coincide with the unique different band reflection locations to create a multiplexed SPR sensor with a different signal on each band detected.

Selective placement, by choice of position as a function of both length and width on the lightpipe surface, of multiple discrete sensor areas (both active and or reference sensing areas) on the external planar lightpipe surfaces creates a matrix of individual channels that can be separately measured by selective detection of a particular angular output band at a selected position along the width of the lightpipe. For example, a matrix of photodetectors can be provided to detect the individual output of angular bands along the width of the lightpipe. Alternatively, a matrix of fiber optic pickups can be utilized to capture the output signals and relay them to a multi-channel spectrograph or a switch and a single channel spectrograph.

Both the first-order and zero-order sensors of this invention can be configured as multi-channel (two or more channels) lightpipe sensors, with sensing areas positioned laterally as illustrated in FIG. 14B. Output light from the different channels is separated along the width of the lightpipe by the placement of sensing areas. Multi-channel lightpipe sensors have two or more sensing channels, one of which is preferably a reference channel. Different sensing channels can be provided with different reactive layers, i.e., functionalized differently, to interact with the same or different species in samples. Two or more of the sensor channels can be functionalized in the same manner to interact and detect the same species in a sample to provide an internal check of SPR measurements.

A multi-channel lightpipe sensor can also be combined with multiple sample flow cells or sample cells having multiple channels, such that different samples interface with different sensing channels.

The first-order sensors of this invention which have angular output bands, as shown in FIGS. 4–6, can be configured as multiplexed sensors with each angular band sensing different analytes. The first-order sensors of this invention can also be configured with a matrix of sensing areas to allow multiplexed sensing in different channels. Conventional surface layer deposition technology combined with conventional masking techniques can be employed to introduce a matrix or other pattern of sensing areas on the lightpipe surface.

The SPR sensors of this invention, and particularly those exemplified in FIGS. 3A, 7 and 9A, can be employed as zero-order sensors by using monochromatic input light (or substantially monochromatic input light) and an appropriate detector for monochromatic light, for example, a linear detector array can be used to measure intensity vs. angular position.

The SPR sensor configuration of this invention can be operated in either angular modulation mode, wavelength modulation mode or a combination of both modes of operation. The light sources employed with the sensor can be monochromatic or more preferably are non-monochromatic. A monochromatic light source provides light of substantially one wavelength. A non-monochromatic light source is any light source that provides light of more than one wavelength, i.e., any light source that provides multiple wavelengths. Preferably, the non-monochromatic source provides a range of wavelengths of light sufficiently broad to encompass the SPR spectrum of the sample. A black body radiation source or one or more broad spectrum light emitting diodes are, for example, suitable multi-wavelength light sources. Alternatively, two or more discrete wavelengths of light, e.g., from distinct light sources, can be employed in the sensor of this invention.

A variety of monochromatic and non-monochromatic sources of incident radiation are readily available. Monochromatic sources include laser sources, e.g., diode lasers, and gas discharge sources. In addition, a monochromatic source can be generated by coupling of white light or other multiple wavelength source with a wavelength selective filter or with a monochromator. Non-monochromatic sources include combinations of two or more monochromatic sources including, one or more LED's, arc sources, black body sources, and certain gas discharge sources, e.g., neon indicator lamps. A tungsten halogen lamp, for example, is a suitable white light source. Best results are obtained when the current in, and temperature of, the white light source are controlled in order to minimize any background spectral variation.

A variety of detector schemes applicable to analysis of the output light of the sensors of this invention are known and readily available to those in the art, including spectrographs, fixed linear array detectors, CCDs (charge coupled devices), photodiode arrays, monochromators, mechanically tunable wavelength output and a single detector, electronically tunable filters (scanning etalon), dispersing prisms and wedge etalons. For example, a photodetector can be combined with a series of bandpass filters, e.g., a filter wheel. Passage of the light exiting the lightpipe through a filter wheel allows selection by rotation of the wheel of a narrow bandpass of the light for wavelength-selective intensity measurement with the photodetector. Detection systems can alternatively employ a dispersing prism, linear variable interference filters or individual interference filters when only a limited number of wavelengths are of interest.

U.S. Pat. No. 5,374,563 describes SPR sensors that employ phase modulation detection. Nelson, S. G. et al. (1996) "High Selectivity Surface Plasmon Resonance Sensor Based on Phase Detection" presented at the Sixth International Conference on Chemical Sensors (Jul. 22–24, 1996) Washington, D.C. also described SPR sensor configurations that employ phase modulation detection. One particular difference in the use of phase modulation is that the input light comprises TM and TE polarized light. The SPR sensors of this invention can be modified or adapted in view of these references and what is known in the art about SPR and phase modulation to employ phase modulation detection, particular those methods specifically described in the cited references.

An anamorphic lens beam expander, which is a lens system that magnifies a beam of light in only one direction, can be employed in the input or output optics of the SPR sensors of this invention. These lens systems are particularly useful for input into lightpipe sensors having a plurality of sensing areas across the width of the lightpipe.

In general, lens and related components employed to collimate or focus light into the SPR sensor configurations or out of the sensor of this invention are preferably achromatic.

The range of RI that can be measured with a given sensor depends upon incident angle, substrate RI, wavelengths of illumination/detection, choice of sensing metal, dynamic range controlling layer and to some extent the metal thickness. RI values above $n_{glass}$ can only be detected when using a dynamic range controlling layer.

The term "substantially" has been used to modify several absolute terms herein, e.g., substantially single angle, substantially collimated, substantially parallel and substantially monochromatic. The term is used to indicate that some deviation from the absolute is tolerated in the configurations described herein. In some cases, for example, in "substantially collimated", the term indicates that it is not, in a practical sense, possible to achieve absolute, i.e., perfectly collimated light. This is appreciated and understood by those in the art. Thus, in the "single angle" configurations of this invention imperfections in collimation of input light will lead to a small range of incidence angles at the sensing area and the configuration will only be substantially single angle.

The term "analyte" is used herein generically to refer to any chemical or biological molecule (nucleic acid, antibody, antigen, blood factor or component, etc.) that is to be detected. The devices and methods of this invention can be used for the quantitative or qualitative detection of one or more analytes in gas or liquid samples. The device and methods of this invention can be employed in the analysis of a solid sample or of a thin film in contact with the sensing area.

The sensors of this invention can be employed in a variety of applications. In general, they can be employed in any application which currently employs a prism or waveguide SPR sensor configuration. These sensors can be adapted as discussed above for use in biological sensing applications, e.g., as biosensor, or use in flow or static sample systems. They will be particularly useful in low cost applications, such as hand-held SPR instrumentation. Specific examples of applications include use as a detector in instrumental effluent stream, such as in HPLC methods or for the detection of corrosion of metals.

The SPR sensors of this invention are useful in industrial process control applications, such as environmental waste stream monitoring, in pharmaceutical production and in food and beverage production.

The sensors of this invention can be employed in combination with other analytical methods including, for example, electrochemical methods. In particular, the sensors of this method can be employed in the combined electrochemical and SPR methods that have been described, for example in methods described in U.S. Pat. No. 4,889,427; in Gordon, J. G. and Ernst, S. (1980) *Surface Science* 101:499–506 and in U.S. provisional patent application Ser. No. 60/007,026, filed Oct. 25, 1995 and corresponding U.S. patent application (Attorney Docket No. 90-95) filed Oct. 25, 1996, all of which are incorporated by reference herein for their disclosure of combined electrochemical and SPR methods.

U.S. Pat. No. 5,485,277 discloses the use of SPR sensors for enhanced fluorescence measurements. The methods disclosed combine a fluorescence detector positioned with respect to the SPR metal layer to detect fluorescence from the layer. SPR sensors of this invention can be readily adapted with appropriate fluorescence detectors for use in such methods.

U.S. Pat. No. 5,313,264 describes the use of an optical multi-analyte sensor system based on internal reflection of polarized light in combination with detection methods based on the evanescent wave phenomenon at TIR including SPR, critical angle refractometry, TIR fluorescence, TIR phosphorescence, TIR light scattering and evanescent wave ellipsometry. The SPR sensors of this invention can be readily adapted or modified in view of the disclosures herein, in U.S. Pat. No. 5,313,264 and in view of methods, techniques and devices that are well-known in the art, for use in combination with TIR-based detection systems, particularly those mentioned above.

EXAMPLES

Example 1

A partially optimized sensor with the sensing area located as shown by the shading in FIGS. 4 and 5 was fabricated on a 28.4 mm long by 0.94 mm thick float glass microscope slide. The sensor was configured as shown in FIG. 3A, with water as the sample. The water sample was retained on slide by surface tension. Individual angular bands of light exiting the light pipe were individually focused using a 20 mm focal length achromatic lens onto a 400 $\mu$m optical fiber and measured with a fiber optic spectrograph to obtain the surface plasmon resonance spectrum of the water sample. Light from the light source was passed through a TM polarizer before passing into the cylindrical lens. The spectrum of the TM polarized light was normalized using the nonresonant TE polarized spectrum to remove the lamp spectrum.

The polarizer was rotated so the light in the system was TE relative to the sensing surface. The spectrum for a band was acquired. Then the polarizer was rotated 90° so the light in the sensor was TM relative to sensing layer and the water resonance was obtained. Then each wavelength intensity value from TM light was divided by the same wavelength intensity value from the TE light. The resonance spectra shown in FIG. 3B are the normalized spectra (light intensity as a function of $\lambda$) for bands 5, 7, and 9 from this sensor configuration and each represents the average reflected output over a small range of incidence angles. The data collected provide resonances for the same sample at a number of incidence angles. If the individual bands are calibrated, these data provide dispersive RI data for the same sample at several different wavelengths Example 2

An experimental sensor like that of FIG. 9 was fabricated with a 0.94 mm thick float glass microscope slide A sensing area formed with a base metal layer of 302 Å of silver with an overcoat of 203 Å of gold deposited on the top surface of the slide. The sensor lightpipe was 70.59 mm long and had an 11.0 mm long metal sensing area extending the width of the planar lightpipe starting 24.5 mm from the input end (from 24.5 mm to 35.5 mm).

The sensor employed a TM polarized white light source. Polarized white light was collimated as a 5 mm beam which was focusing onto the bottom planar side of the light pipe through a cylindrical lens. The illuminated spot sizes along the top surface of the substrate were approximately 5 mm wide, with lengths according to the illumination pattern in FIG. 5. Light passing through the lightpipe and reflecting off of the sensing area excited surface plasmon waves on the metal surface and was then reflected out of the sensor by the diffraction grating index matched onto the output bevel. The grating was oriented to disperse each band out of the page. The exiting bands of light were collimated with a second cylindrical lens, and the dispersed wavelengths were imaged with a third cylindrical lens onto a white paper screen placed a the output plane to produce an image of reflected light intensity versus angle and wavelength. The plot in FIG. 9B illustrates an idealized contour plot of the TM reflection coefficient as a function of both wavelength and angle. Note that the output of the illustrated sensor is modulated by the odd numbered angular bands of light. The complementary pattern produced by the even bands missed the output optics and therefore were not captured or collimated.

The angular response of the system was calibrated by measuring the dimensions of the lightpipe with a micrometer and calculating the angles according to the previously described ray theory. The wavelength response was calibrated using various bandpass filters with center wavelengths of 480 through 660 nm. A CCD (charge coupled display) camera with a macro lens was used to detect the image on the white screen. A dark frame with the lamp off was acquired with the camera to account for thermal noise in the camera and stray background light. A nonresonant reference image to represent the lamp spectrum was acquired using TM light and a sample of air, which has an index too low to support SPR in this configuration. The dark frame was subtracted from both the reference and the sample images, and then the sample image was divided by the reference. For samples of acetone and water, the wavelength modulated spectra of the six brightest angular bands corresponding to the odd bands 13 through 23 were acquired using an image processing tool to analyze regions of the normalized image.

The reflection spectra obtained from the odd bands exiting the lightpipe were found to be extremely noisy due to the data acquisition method employed. The noise observed can be significantly decreased by imaging directly into a CCD camera. Six spectra were analyzed to find $\lambda_{spr}$ for each band. Although the first order nature of the sensor makes it possible to utilize statistical calibration techniques (Martens, H. and Naes, T. (1989), *Multivariate Calibration,* John Wiley and Sons), a classical analysis of the location of the resonant wavelength for each angular band of the output was performed. The resonance minima were determined by boxcar averaging of the collected experimental data to reduce noise, and then fitting a parabola to the data curve and mathematically determining the location of the minimum of the parabola. The sensor response was modeled with the multilayer Fresnel reflection equations (Ishimaru, A. (1991) *Electromagnetic Wave Propagation, Radiation, and Scattering,* (Prentice Hall, New Jersey), p. 43), using dispersive RI data for BK7 *Schott Optical Glass Catalog,* (1992), (Schott Glass Technologies, Inc., Duryea, Pa.) to represent the float glass light pipe, 302 Å of silver (Gray, D. E. (Ed.) (1972), *American Institute of Physics Handbook,* 3rd ed., McGraw-Hill, New York, section 6, p. 149), 203 Å of gold (Gray, D. E. (Ed.), *American Institute of Physics Handbook,* 3rd ed., McGraw-Hill, New York, section 6, p. 138), and bulk dielectric samples of acetone (Gray, D. E. (Ed.), *American Institute of Physics Handbook,* 3rd ed., McGraw-Hill, New York, section 6, p. 105) and water (Palik, E. D. (Ed.) (1985), *Handbook of Optical Constants of Solids,* Academic Press, Orlando, p. 1071). The measured center angles of each band are plotted against $\lambda_{spr}$ in FIG. 10 and compared to values calculated using the model. FIG. 10 shows that $\Delta\lambda_{spr}/\Delta RI$ measured using the sensor closely matches values predicted by theory. For the 9.9° band the sensitivity is approximately 31 nm per 0.025 refractive index units (RIU) or, when inverted, $8.1\times10^{-4}$ RIU/nm. The discrepancy between the model and the experimental data is primarily due to systematic error resulting from differences in the dispersive RI values used in the model calculation from their actual values (published RI values for BK7 were lower than those of the float glass of used for the experimental lightpipe substrate) and to the experimental uncertainty of the focus position on the center of the input face. There was also some uncertainty in determining the experimental values of $\lambda_{spr}$ due to broad resonance curves and noise on the acquired spectra.

Example 3

A one-angle SPR symmetrical lightpipe sensor system, as shown in FIG. 11, was fabricated using a standard 25 mm wide microscope slide as the lightpipe. The slide was cut to a length of L=72.2 mm. Two metalized bevels were polished with angles of $\alpha=36°$ which corresponds to an incidence angle $\theta=72°$. To support SPR, a 49.9 nm (499 Å) thick gold layer was deposited on the top of a 2 nm (20 Å) Cr adhesion underlayer to form the sensing area. The sensing area was 5 mm long (l=5 mm) and 10 mm wide and position ed symmetrically along the length and width of the top surface of the lightpipe. A flow cell with a gasket seal was positioned over the metal sensing area on the top surface of the lightpipe was built to confine samples to the sensing area. Input light (white light) from a 100 watt halogen bulb (Oriel, Model 77501) was transmitted to the sensor by a 400 µm diameter optical fiber and collimated by a 10 mm focal length achromatic lens. The collimated light was TM polarized before it was coupled into the lightpipe. An identical collimator was used to collect the reflected light into an optical fiber and conducted it to the spectrograph detector.

Glycerol solutions of known concentrations were used as chemical samples in experiments to demonstrate the performance of the SPR one-angle lightpipe sensor. The SPR reflection spectra of these glycerol solutions were obtained using the planar lightpipe described above by dividing each output spectrum with a TE reference spectrum. The TE polarized component of the light does not excite SPR and serves as a simple way to record the spectrum of the lamp, fiber and detector. The normalized SPR reflection spectra for 4 different glycerol solutions are shown in FIGS. 12(a)–12(d).

The SPR resonance wavelength was determined from the SPR reflect ion spectrum by boxcar smoothing and parabolic curve fitting around the reflection minimum of each spectrum. The calibration curve for SPR resonance wavelength and glycerol concentration by weight in solution was determined by least squares curve fitting of concentration of glycerol solutions versus SPR resonance wavelength. The calibration was found to be substantially linear over the concentration rang e examined (0.59%–16.02% by weight), see FIG. 13. Published values of the refractive indexes of aqueous glycerol solutions of different concentrations are shown on the alternate axis in FIG. 13 to demonstrate the corresponding RI calibration (Weast, R. C. (Ed.), (1985–1986) "CRC *Handbook of Chemistry and Physics,* 66th ed., CRC Press, Inc., Boca Raton, Fla.

Figure 13:
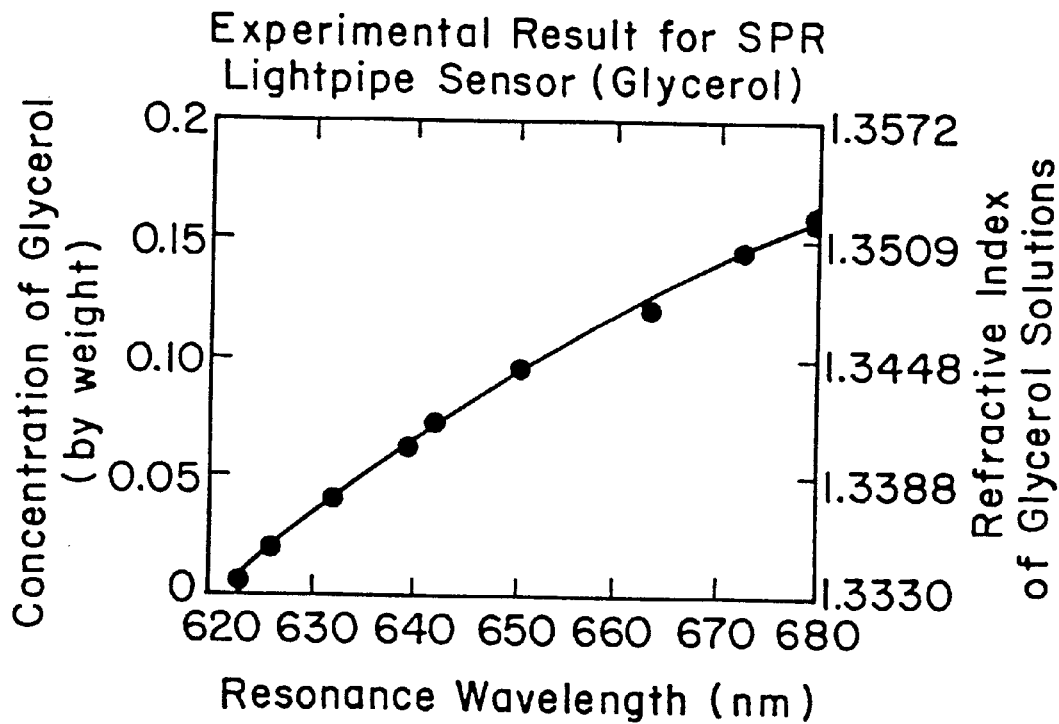
FIG. 13 is a graph of SP resonance wavelength ($\lambda_{SPR}$) of aqueous glycerol solutions as a function of concentration (weight percent of solution) showing the linear calibration curve for a sensor of FIG. 12. The corresponding refractive indices of the solutions are shown on the alternate axis. Experimental points are indicated by "*" and the solid line indicates curve fitting.

The stability of the one-angle SPR lightpipe sensor was assessed by measuring the fluctuation of the SPR resonance wavelength for each glycerol solution of FIG. 13 over a 10 minute period. The short term test results, not shown, indicated excellent short term stability.

Longer stability experiments showed that the standard deviation of the SPR resonance wavelength ($\sigma_{spr}$) over a two hour period is on the order of $\sigma_{spr}$=0.1 nm. The standard deviation of the SPR resonance wavelength fluctuation over time can be used to predict the refractive index sensitivity of the lightpipe SPR sensor system. The local derivative of the refractive index calibration shown in FIG. 13 was multiplied by $\sigma_{spr}$ to find the smallest resolvable change in RI ($\sigma_n$). The estimated value of $\sigma_n$ for an RI around 1.345 is on the order of $\sigma_n$=4×10$^{-5}$. The same technique applied to the concentration calibration yields a sensitivity value of $\sigma_{conc(wt)}$ of 3.4×10$^{-4}$ (weight %).

Example 4

A Multiple-Channel SPR Lightpipe Sensor

The beveled-ended zero order configuration of FIG. 11 was designed to have a dual channel lightpipe sensor as shown in FIG. 15. A standard 25 mm wide microscope slide was cut to a length of 72.2 mm and divided lengthwise into two channels adjacent to each other as shown in FIG. 14A. A sensing area was fabricated on the top surface of the lightpipe by electron beam evaporation of a 2 nm thick Cr adhesion layer followed by a 50 nm thick gold SPR-supporting layer. The sensing area was 5 mm long and 20 mm wide. A flow cell with a gasket (not shown) carried samples to the sensing area. In this particular case, both sensing channels have identical sensing areas. Output from the two different sensing channels, at different positions along the width of the lightpipe, exited the lightpipe at corresponding positions along the width of the lightpipe and was separately collected and analyzed in a detector system. White input light from a 100 W halogen bulb (Oriel, Model 77501) was TM polarized and transmitted to the lightpipe by an optical fiber. Input light was then collimated using a 15 mm focal length achromatic lens and coupled in to the lightpipe through the bottom surface by reflection off of the beveled input end ($\alpha$=36°). The input light was shared by both channels, i.e. distributed across the width of the lightpipe. In this case, the diameter of the lens was selected so that a sufficiently large width of the input face was illuminated to allow input light to interact with both sensing channels.

Both sensing channels were contacted with the same samples, a series of aqueous glycerol solutions ranging in concentration from 0.0%–30% (by weight), and both sensing channels were maintained at constant temperature, 25° C. The literature values for the RI's of the samples ranged from 1.334 to 1.369.

If the input beam is not perfectly collimated, light at a range of incident angles interacts with and excites SPR in the sensing area. An input beam can be uncollimated to a given consistent degree by offsetting an input fiber from the focal point of the lens. As in the lightpipe sensor of FIG. 3A, the output is a set of angular bands, and different angular bands contain SPR spectra excited at different incident angles.

Figure 16A:
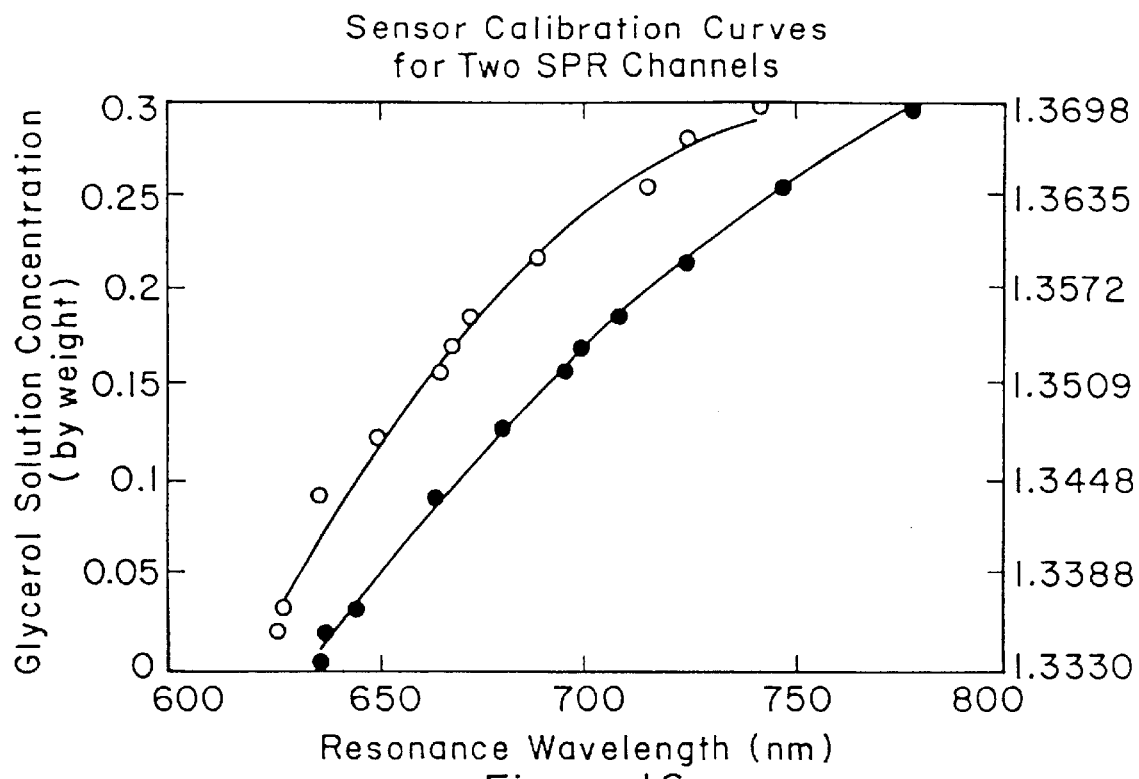
FIG. 16A is a graph of $\lambda_{SPR}$ measured at both channels of the dual-channel SPR sensor of FIG. 14 as a function of glycerol concentration.
Figure 16B:
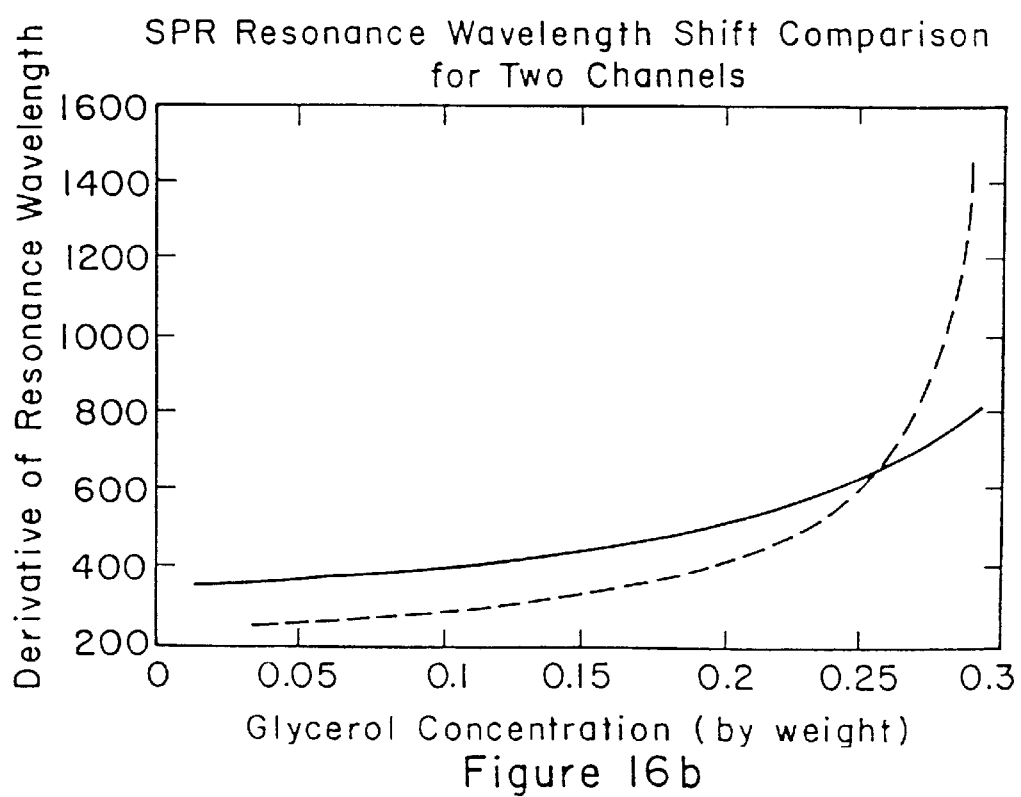
FIG. 16B is a graph in which the derivatives of the concentration curve ($\delta\lambda_{SPR}/\delta_{conc}$) of FIG. 16A are plotted as a function of glycerol concentration to compare the SPR signal shifts due to the refractive index variations in the spectra from two channels representing two different incidence angles on the sensing surface.

To demonstrate that two different SPR spectra can be obtained from adjacent channels on the lightpipe surface, the SPR spectra from the two channels for two different incidence angles (i.e., of two different angular bands) were measured. The SPR reflection spectra of the aqueous glycerol solutions were obtained by channel selective detection of the output spectra of different angular output bands and dividing each output spectrum by the TE polarized component of the light. (This corrects for the spectrum of the light, fiber and detector.) The SPR wavelength ($\lambda_{SPR}$) was determined from these reflection spectra by boxcar smoothing and parabolic curve fitting around the reflection minimum of each spectrum. The relationship between $\lambda_{SPR}$ and glycerol concentration of both channels was determined by using a least square curve fitting as shown in FIG. 16A. The derivatives of the concentration curve ($\delta\lambda_{SPR}/\delta$conc) are plotted as a function of glycerol concentration in FIG. 16B to compare the SPR signal shifts due to the refractive index variations in the spectra from two channels (different incidence angles). The concentration calibration curves of the two channels are different. This confirms that the output of the two channels can be separately measured and analyzed. Analogously, SPR signal shifts derived from the output of the two different channels from the same angular band are substantially the same (not shown). Consequently, in an analogous dual-channel lightpipe sensor, if one of the sensing areas is activated and the other is not, the non-activated sensing area can be used as a source of a reference signal to compensate for system variables including temperature variation.

Those of ordinary skill in the art will appreciate that methods, materials and techniques other than those specifically discussed herein can be readily employed or adapted to implement the sensor configurations and practice the methods of this invention. For example, a variety of means for measuring reflection coefficients and/or light intensity, particular as a function of wavelength, are well-known and available to those in the art. In addition, there are a variety of techniques and devices known for collimating, collecting, focusing and conducting light that can be applied or readily adapted to light input to or light output from the sensors of this invention. Those of ordinary skill in the art can readily select from among such alternatives, variants and functional equivalents those that are appropriate for use in the SPR configuration of this invention.

All of the references cited in this specification are incorporated by reference in their entireties herein.

We claim:

1. A surface plasmon resonance sensor which comprises:
   a planar lightpipe having an input end, an output end and a sensing area on an external planar surface, said sensing area comprising a conducting layer that supports surface plasmon resonance;

a light source optically connected to the input end of said lightpipe to introduce light into said lightpipe at a range of angles such that the light is conducted through said lightpipe by total internal reflection to reflect off said sensing area, exciting a surface plasmon wave therein, and to exit said lightpipe at said output end in angular bands, each of said bands caused by a different number of reflections of said light in said lightpipe;

a detector for receiving a plurality of angular bands of light exiting said output end and reflected from said sensing area which thereby detects surface plasmon resonance.

2. The sensor of claim 1 wherein said light source is a multiple wavelength light source.

3. The sensor of claim 2 wherein light is introduced into said lightpipe by focusing said light at the input end of the lightpipe.

4. The sensor of claim 2 wherein said light is introduced asymmetrically at a range of angles filling angles on only one side of the optical axis of the lightpipe.

5. The sensor of claim 2 wherein said light is introduced into said lightpipe at a range of angles filling angles on either side of the optical axis of the lightpipe.

6. The sensor of claim 2 wherein said lightpipe comprises two or more sensing areas on a planar surface.

7. The sensor of claim 6 wherein one of said sensing areas is a reference sensing area.

8. The sensor of claim 6 wherein said lightpipe comprises a plurality of sensing areas across the width of the lightpipe.

9. The sensor of claim 6 wherein said lightpipe comprises a plurality of sensing areas along the length of the lightpipe.

10. The sensor of claim 2 wherein said sensing area comprises a surface plasmon resonance-supporting metal layer.

11. The sensor of claim 10 wherein said sensing area comprises an adherence layer.

12. The sensor of claim 10 wherein said sensing area comprises a reactive layer.

13. The sensor of claim 12 comprising a plurality of sensing areas along the width of the lightpipe and wherein at least one of said sensing areas is a reference sensing area.

14. The sensor of claim 13 wherein said sensing areas that are not reference sensing areas each comprise a reactive layer.

15. The sensor of claim 14 wherein in each of said sensing areas comprising a reactive layer, the reactive layer is specific for a different analyte.

16. The sensor of claim 12 wherein the sensor is a biosensor.

17. The sensor of claim 2 wherein the detector is a spectrograph.

18. The sensor of claim 2 wherein the detector is a CCD camera.

19. The sensor of claim 2 wherein the detector comprises a fiber optic pickup.

20. The sensor of claim 2 which comprises a telecentric lens optically coupled to the output end of said lightpipe.

21. The sensor of claim 20 wherein said telecentric lens is a cylindrical telecentric lens.

22. The sensor of claim 20 wherein said telecentric lens is a spherical telecentric lens.

23. The sensor of claim 22 wherein angular bands of light exiting said lightpipe are redirected and focused by said telecentric lens to be substantially parallel to the optic axis of the lens.

24. The sensor of claim 2 wherein the input end of the lightpipe is beveled.

25. The sensor of claim 24 wherein input light is focused at the external face of the beveled input end.

26. The sensor of claim 25 wherein both the input and output end of the lightpipe are beveled.

27. The sensor of claim 26 wherein the reflective surface of the bevel comprises a diffraction grating.

28. The sensor of claim 24 wherein said input and output ends are beveled at 45° with respect to the normal to the bottom surface of the lightpipe.

29. The sensor of claim 28 wherein input light is focused at the internal face of said beveled input end through the bottom planar surface of the lightpipe.

30. The sensor of claim 2 further comprising a sample cell adjacent to said lightpipe sensor which allows a gas or liquid sample to interface with a sensing area of the lightpipe.

31. The sensor of claim 30 wherein said sample cell is a flow cell.

32. The sensor of claim 2 further comprising a TM polarizer optically coupled anywhere within said sensor to exclude TE polarized light from said detector.

33. The sensor of claim 2 further comprising a first cylindrical lens optically coupled between said light source and the input face of said lightpipe which focuses light passing there through at the input face of the lightpipe at a range of angles.

34. The sensor of claim 33 further comprising a second cylindrical lens optically coupled between said light source and the said first cylindrical lens, wherein said second cylindrical lens collimates light across width of the lightpipe.

35. The sensor of claim 2 wherein said lightpipe is fabricated from glass or crystal.

36. The sensor of claim 2 wherein said lightpipe is substantially coated with a cladding layer having an index of refraction different from that of the lightpipe substrate except that the cladding does not cover said sensing area.

37. The sensor of claim 2 wherein said lightpipe is fabricated from plastic or a polymer material.

38. The sensor of claim 37 wherein said lightpipe is substantially coated with a cladding layer having an index of refraction different from that of the lightpipe substrate except that the cladding does not cover the sensing area.

39. A method for surface plasmon resonance measurement of a sample, which method comprises the steps of contacting the sample with a sensing area of a surface plasmon resonance lightpipe sensor of claim 2 and detecting the reflection spectrum of an angular band of light exiting said lightpipe.

40. A method for surface plasmon resonance measurement of a plurality of analytes in a sample, which method comprises the steps of contacting the sensing areas of an surface plasmon resonance lightpipe sensor of claim 8 with the sample and detecting the reflection spectrum of angular bands of light exiting said lightpipe.

41. A method for surface plasmon resonance measurement of a plurality of analytes in a sample, which method comprises the steps of contacting the sensing areas of an surface plasmon resonance lightpipe sensor of claim 9 with the sample and detecting the reflection spectrum of angular bands of light exiting said lightpipe.

42. The method of claim 2 wherein said sensing area of said lightpipe is positioned within about the first 20% of the length of the lightpipe as measured from the input end of the lightpipe.

43. A surface plasmon resonance sensor which comprises:
a planar lightpipe having an input end, an output end and a sensing area on an external planar surface, said sensing area comprising a conducting layer that supports surface plasmon resonance;

a non-monochromatic light source optically connected to the input end of said lightpipe to introduce light into said lightpipe at a range of angles such that the light is conducted through said lightpipe by total internal reflection to reflect off said sensing area, exciting a surface plasmon wave therein, and to exit said lightpipe at said output end in angular bands each of said bands caused by a different number of reflections of said light in said lightpipe;

a detector for receiving a plurality of angular bands of light exiting said output end and reflected from said sensing area which thereby detects surface plasmon resonance.

44. The sensor of claim 43 wherein said detector can receive angular bands exiting said output end both above and below the optical axis of said lightpipe.

45. A method for surface plasmon resonance measurement of a sample, which method comprises the steps of contacting a sensing area of a surface plasmon resonance lightpipe sensor of claim 43 with said sample and detecting a reflection spectrum of a plurality of angular band of light exiting said lightpipe.

46. The method of claim 45 wherein detecting a reflection spectra of a plurality of angular bands of light exiting said lightpipe provides a determination of the wavelength dependent permivitity of said sample.

* * * * *

UNITED STATES PATENT AND TRADEMARK OFFICE
CERTIFICATE OF CORRECTION

PATENT NO. : 5,991,048

DATED : Nov. 23, 1999

INVENTOR(S) : Karlson et al.

It is certified that error appears in the above-identified patent and that said Letters Patent is hereby corrected as shown below:

On the title page:
At [56], OTHER PUBLICATIONS, please insert
--Ruiz, E. Garcia et al. (1993), "Industrial process sensor based on surface plasmon resonance (SPR) 1. Distillation process monitoring." *Sensors and Actuators A* 37-38:221-225.
Smith, W. J. (1992), *Modern Optical Engineering, The Design of Optical Systems*, $2^{nd}$ ed. (McGraw Hill), p. 192-195, 263-265.--

In column 4, line 45, please replace "$A_{b,r}$" with --$A_{b,r}$--.

In column 4, line 46, please replace "$B_{b.5}$" with --$B_{b,r}$--.

In column 4, lines 54 and 55, please replace "The shaded area is" with --The two vertical lines at approximately 20% and 60% of length mark--.

In column 5, line 25, after "water." please insert:
--Experimental points for acetone and water are respectively indicated by "□" and "+." Theoretical calculations for acetone and water are respectively indicated by solid and broken lines--.

UNITED STATES PATENT AND TRADEMARK OFFICE
CERTIFICATE OF CORRECTION

PATENT NO. : 5,991,048

DATED : Nov. 2,3 1999

INVENTOR(S) : Karlson et al.

It is certified that error appears in the above-identified patent and that said Letters Patent is hereby corrected as shown below:

In column 5, line 42, please replace "*" with --•--.
In column 11, line 39, after "with thick" please insert --white--.
In column 11, line 41, after "with thin" please insert --black--.
In column 11, line 52, please replace "Figure 3B" with --Figure 3C--.
In column 12, line 9, please replace "lens" with --lenses--.
In column 13, line 11, please replace "angel" with --angle--.
In column 13, line 47, please delete "(41)".
In column 20, line 45, please replace "lenses," with --lens,--.
At claim 40, column 30, line 51, please replace "an" with --the--.
At claim 41, column 30, line 57, please replace "an" with --the--.
At claim 45, column 32, line 8, please replace "band" with --bands--.
At claim 46, column 32, line 11, please replace "spectra" with --spectrum--.

Signed and Sealed this

Twenty-second Day of August, 2000

Attest:

Q. TODD DICKINSON

*Attesting Officer*   *Director of Patents and Trademarks*

UNITED STATES PATENT AND TRADEMARK OFFICE
CERTIFICATE OF CORRECTION

PATENT NO. : 5,991,048

DATED : Nov. 23, 1999

INVENTOR(S) : Karlson et al.

It is certified that error appears in the above-identified patent and that said Letters Patent is hereby corrected as shown below:

On the cover page at [75], please rewrite the first inventor's surname, "Karlson" as --Karlsen--.

Signed and Sealed this

Twenty-fourth Day of October, 2000

Attest:

Q. TODD DICKINSON

*Attesting Officer*  *Director of Patents and Trademarks*